(12) United States Patent
Kaplan et al.

(10) Patent No.: US 10,653,786 B2
(45) Date of Patent: May 19, 2020

(54) SILK MICROSPHERES AND METHODS FOR SURFACE LUBRICATION

(71) Applicants: Trustees of Tufts College, Medford, MA (US); The Administrators of the Tulane Educational Fund, New Orleans, LA (US)

(72) Inventors: David L. Kaplan, Concord, MA (US); Xiaoqin Wang, Winchester, MA (US); Vijay John, New Orleans, LA (US); Noshir Pesika, New Orleans, LA (US); Rubo Zheng, New Orleans, LA (US)

(73) Assignees: TRUSTEES OF TUFTS COLLEGE, Medford, MA (US); Tulane Educational Fund, New Orleans, LA (US)

( * ) Notice: Subject to any disclaimer, the term of this patent is extended or adjusted under 35 U.S.C. 154(b) by 0 days.

(21) Appl. No.: 14/390,351

(22) PCT Filed: Apr. 25, 2013

(86) PCT No.: PCT/US2013/038186
§ 371 (c)(1),
(2) Date: Oct. 2, 2014

(87) PCT Pub. No.: WO2013/163407
PCT Pub. Date: Oct. 31, 2013

(65) Prior Publication Data
US 2015/0150993 A1 Jun. 4, 2015

Related U.S. Application Data

(60) Provisional application No. 61/638,294, filed on Apr. 25, 2012, provisional application No. 61/778,794, filed on Mar. 13, 2013.

(51) Int. Cl.
*A61K 47/42* (2017.01)
*A61K 9/16* (2006.01)
(Continued)

(52) U.S. Cl.
CPC ............ *A61K 47/42* (2013.01); *A61K 9/1617* (2013.01); *A61K 45/06* (2013.01); *A61L 27/227* (2013.01);
(Continued)

(58) Field of Classification Search
CPC ..... A61K 47/42; A61K 9/1617; A61L 27/227; A61L 27/28; A61L 27/3645; A61L 27/50; A61L 27/54
See application file for complete search history.

(56) References Cited

U.S. PATENT DOCUMENTS 5,245,012 A   9/1993 Lombari et al.
5,591,828 A   1/1997 Bosslet et al.
(Continued)

FOREIGN PATENT DOCUMENTS

WO   WO-93/11161 A1   6/1993
WO   WO-97/08315 A1   3/1997
(Continued)

OTHER PUBLICATIONS

Wang et al. J. Controlled Release. Silk microspheres for encapsulation and controlled release. 2007, 117:360-370.*
(Continued)

*Primary Examiner* — Lakshmi S Channavajjala
(74) *Attorney, Agent, or Firm* — Quarles & Brady LLP

(57) ABSTRACT

Provided herein relates to compositions and methods for lubrication of a surface. The surface amenable to the compositions and methods described herein can be a non-biological surface, a biological surface, or a combination thereof. In some embodiments, the composition comprising (Continued)

a phospholipid-coated silk microsphere can be used for lubrication of a surface. In some embodiments, the composition comprising a phospholipid-coated silk microsphere can be used for joint lubrication, e.g., for treatment of joint disorders such as arthritis.

24 Claims, 22 Drawing Sheets

(51) Int. Cl.
  *A61L 27/50*  (2006.01)
  *A61L 27/28*  (2006.01)
  *A61L 27/36*  (2006.01)
  *A61L 27/54*  (2006.01)
  *A61L 27/22*  (2006.01)
  *A61K 45/06*  (2006.01)

(52) U.S. Cl.
  CPC ............ *A61L 27/28* (2013.01); *A61L 27/3645* (2013.01); *A61L 27/50* (2013.01); *A61L 27/54* (2013.01); *A61L 2300/622* (2013.01); *A61L 2400/10* (2013.01); *A61L 2430/24* (2013.01)

(56) References Cited

U.S. PATENT DOCUMENTS

| | | | |
|---|---|---|---|
| 6,287,340 | B1 | 9/2001 | Altman et al. |
| 7,842,780 | B2 | 11/2010 | Kaplan et al. |
| 8,283,333 | B2 | 10/2012 | Yaworski et al. |
| 8,715,740 | B2 * | 5/2014 | Wang ............... A61K 9/5169 264/4.1 |
| 2002/0001716 | A1 * | 1/2002 | Barbera-Guillem ... B82Y 15/00 428/402.24 |
| 2004/0005352 | A1 * | 1/2004 | Lopez ............... A61K 9/1272 424/450 |
| 2005/0123593 | A1 | 6/2005 | Thompson et al. |
| 2006/0273279 | A1 * | 12/2006 | Kaplan ............... A61L 27/227 252/1 |
| 2007/0212730 | A1 | 9/2007 | Vepari et al. |
| 2009/0232963 | A1 | 9/2009 | Kaplan et al. |
| 2010/0028451 | A1 * | 2/2010 | Kaplan ............... A61K 9/1658 424/491 |
| 2010/0098749 | A1 | 4/2010 | Barenholz et al. |
| 2010/0178304 | A1 | 7/2010 | Wang et al. |
| 2010/0279112 | A1 | 11/2010 | Kaplan et al. |
| 2011/0008406 | A1 | 1/2011 | Altman et al. |
| 2011/0171239 | A1 | 7/2011 | Kaplan et al. |
| 2011/0172768 | A1 | 7/2011 | Cragg et al. |
| 2012/0171770 | A1 | 7/2012 | Numata et al. |
| 2015/0056294 | A1 | 2/2015 | Kaplan et al. |

FOREIGN PATENT DOCUMENTS

| | | |
|---|---|---|
| WO | WO-04/000915 A2 | 12/2003 |
| WO | WO-04/001103 A2 | 12/2003 |
| WO | WO-04/062697 A2 | 7/2004 |
| WO | WO-2005/000483 A1 | 1/2005 |
| WO | WO-2005/012606 A2 | 2/2005 |
| WO | WO-2005/123114 A2 | 12/2005 |
| WO | WO-2006/042287 A2 | 4/2006 |
| WO | WO-2006/076711 A2 | 7/2006 |
| WO | WO-2007/016524 A2 | 2/2007 |
| WO | WO-2007/098951 A2 | 9/2007 |
| WO | WO-2007/103442 A1 | 9/2007 |
| WO | WO-2008/085904 A1 | 7/2008 |
| WO | WO-2008/106485 A2 | 9/2008 |
| WO | WO-2008/108838 A2 | 9/2008 |
| WO | WO-2008/118133 A2 | 10/2008 |
| WO | WO-2008/118211 A2 | 10/2008 |
| WO | WO-2008/127401 A2 | 10/2008 |
| WO | WO-2008/127402 A2 | 10/2008 |
| WO | WO-2008/127403 A2 | 10/2008 |
| WO | WO-2008/127404 A2 | 10/2008 |
| WO | WO-2008/127405 A2 | 10/2008 |
| WO | WO-2008/140562 A2 | 11/2008 |
| WO | WO-2008/150861 A1 | 12/2008 |
| WO | WO-2009/061823 A1 | 5/2009 |
| WO | WO-2009/100280 A2 | 8/2009 |
| WO | WO-2009/126689 A2 | 10/2009 |
| WO | WO-2009/140588 A1 | 11/2009 |
| WO | WO-2009/155397 A2 | 12/2009 |
| WO | WO-2010/040129 A2 | 4/2010 |
| WO | WO-2010/042798 A2 | 4/2010 |
| WO | WO-2010/141133 A2 | 12/2010 |
| WO | WO-2011/005381 A2 | 1/2011 |
| WO | WO-2011/006133 A2 | 1/2011 |
| WO | WO-2011/008842 A2 | 1/2011 |
| WO | WO-2011/011347 A2 | 1/2011 |
| WO | WO-2011/041395 A2 | 4/2011 |
| WO | WO-2012/145739 A1 | 10/2012 |

OTHER PUBLICATIONS

Wang et al 2. Biomaterials. Silk nanospheres and microspheres from silk/PVA blend films for drug delivery. 31(6):1025-1035.*
Cotellier et al. Protein encapsulation in liposomes: efficiency depends on interactions between protein and phospholipid bilayer. BMC Biotechnology May 10, 2002, 2:9 pp. 1-8 (Year: 2002).*
Abate, M. et al., Viscosupplementation with hyaluronic acid in hip osteoarthritis (a review), Ups. J. Med. Sci., 113(3):261-77 (2008).
Acharya, C. et al., Performance evaluation of a silk protein-based matrix for the enzymatic conversion of tyrosine to $_L$-DOPA, Biotechnol. J., 3:226-233 (2008).
Altman, G.H. et al., Silk-based biomaterials, Biomaterials, 24:401-416 (2003).
Batzer, M.A. et al., Enhanced evolutionary PCR using oligonucleotides with insosine at the 3'-terminus, Nucleic Acids Research, 19(18): 5081 (1991).
Bayraktar et al., Silk fibroin as a novel coating material for controlled release of theophylline, Eur. J. Pharm. Biopharm. 60:373-381 (2005).
Benz, M. et al., Lubrication and wear properties of grafted polyelectrolytes, hyaluronan and hylan, measured in the surface forces apparatus, J. Biomed. Mater Res. A, 71(1):6-15 (2004).
Chothia, C. and Lesk, A.M., Canonical structures for the hypervariable regions of immunoglobulins, Journal of Molecular Biology, 196(4):901-917 (1987).
Corti, M.C. and Rigon, C., Epidemiology of osteoarthritis: prevalence, risk factors and functional impact, Aging Clin. Exp. Res., 15(5):359-63 (2003).
Demura, M. and Asakura, T., Immobilization of glucose oxidase with Bombyx mori silk fibroin by only stretching treatment and its application to glucose sensor, Biotechnology and Bioengineering, 33(5):598-603 (1989).
Grainger, R. and Cicuttini, F.M., Medical management of osteoarthritis of the knee and hip joints, Med. J. Aust., 180(5):232-6 (2004).
Gupta, et al., Fabrication and Characterization of Silk Fibroin-derived Curcumin Nanoparticles for Cancer Therapy, International Journal for Nanomedicine, 4:115-122 (2009).
Hino, T. et al., Silk Microspheres Prepared by Spray-drying of an Aqueous System, Pharmacy Pharmacol. Commun., 6:335-339 (2000).
Hofmann, S. et al., Silk fibroin as an organic polymer for controlled drug delivery, Journal of Controlled Release, 111:219-227 (2006).
Hollinger, P. et al., Diabodies: Small bivalent and bispecific antibody fragments, Proc. Natl. Acad. Sci., 90:6444-6448 (1993).
Hu, X. et al., Regulation of Silk Material Structure by Temperature-Controlled Water Vapor Annealing, Biomacraomolecules, 12:1686-1696 (2011).
International Search Report for PCT/US2013/038186, 4 pages (dated Sep. 27, 2013).
Jin, H. et al., Water-Stable Silk Films with Reduced p-Sheet Content, Advanced Functional Materials, 15:241-1247 (2005).
Kawano, T. et al., Mechanical effects of the intraarticular administration of high molecular weight hyaluronic acid plus phospholipid

(56) References Cited

OTHER PUBLICATIONS on synovial joint lubrication and prevention of articular cartilage degeneration in experimental osteoarthritis, Arthritis Rheum., 48(7):1923-9 (2003).
Li, et al., Study on Porous Silk Fibroin Materials. I. Fine Structure of Freeze Dried Silk Fibroin, J Appl Polym Sci, 79:2185-2191 (2001).
Lu, S. et al., Stabilization of Enzymes in Silk Films, Biomacromolecules, 10:1032-1042 (2009).
Lucas, F. et al., The silk fibroins, Advances in Protein Chemistry, 107-242 (1958).
Min, S. et al., Preparation and Characterization of Crosslinked Porous Silk Fibroin Gel, Sen'l Gakkaishi, 54(2):85-92 (1997).
Miyairi, S. and Sugiura, M., Properties of β-Glucosidase Immobilized in Sericin Membrane, J. Germent. Technol., 56(4):303-308 (1978).
Nazarov, R. et al., Porous 3-D scaffolds from regenerated silk fibroin, Biomacromolecules, 5(3):718-26 (2004).
Numata, et al., Silk-based Delivery Systems of Bioactive Molecules, Advances in Drug Delivery Reviews, 62(15):1497-1508 (2010).
Ohtsuka, E. et al., An alternative approach to deoxyoligonucleotides as hybridization probes by insertion of deoxyinosine at ambiguous codon positions, J. Biol. Chem., 260(5): 2605-2608 (1985).
Oloyede, A. et al., Consolidation responses of delipidized articular cartilage, Clin. Biomech. (Bristol, Avon), 19(5):534-42 (2004).
Park, J.H. et al., The effect of heat on skin permeability, International Journal of Pharmacology, 359(1-2):94-103 (2008).
Pluckthun, A., Antibodies from *Escherichia coli*, The Pharmacology of Monoclonal Antibodies, Rosenburg and Moore eds., Springer-Verlag: New York, Ch. 11, 113:269-315 (1994).
Rossolini, G.M. et al., Use of Deoxyinosine-containing primers vs degenerate primers for polymerase chain reaction based on ambiguous sequence information, Molecular and Cellular Probes, 8(2):91-98 (1994).
Sarma, A.V. et al., Phospholipid composition of articular cartilage boundary lubricant, J. Orthop. Res., 19(4):671-6 (2001).
Schwarz, I.M. and Hills, B.A., Surface-active phospholipid as the lubricating component of lubricin, Br. J. Rheumatol., 37(1):21-6 (1998).
Sivan, S. et al., Liposomes act as effective biolubricants for friction reduction in human synovial joints, Langmuir, 26(2):1107-16 (2010).
Sofia, S. et al., Functionalized silk-based biomaterials for bone formation, Journal of Biomedical Materials Research, 54(1): 139-148 (2001).
Swann, D.A. and Mintz, G., The isolation and properties of a second glycoprotein (LGP-II) from the articular lubricating fraction from bovine synovial fluid, Biochem. J., 179(3):465-71 (1979).
Swann, D.A. et al., The lubricating activity of synovial fluid glycoproteins. Arthritis Rheum., 24(1):22-30 (1981).
Swann, D.A. et al., The molecular structure of lubricating glycoprotein-I, the boundary lubricant for articular cartilage, J. Biol. Chem., 256(11):5921-5 (1981).
Vecchio, P. et al., Surfactant treatment for osteoarthritis. Rheumatology (Oxford), 38(10):1020-1 (1999).
Wang, X. et al., Silk microspheres for encapsulation and controlled release, Journal of Controlled Release, 117(3):360-370 (2007).
Wang, X. et al., Silk nanospheres and microspheres from silk/pva blend films for drug delivery, Biomaterials, 31(6): 1025-1035 (2010).
Wang, X. et al., Sonication-induced gelation of silk fibroin for cell encapsulation, Biomaterials, 29(8):1054-1064 (2008).
Watanabe, M. et al., Ultrastructural study of upper surface layer in rat articular cartilage by "in vivo cryotechnique" combined with various treatments, Med. Electron Microsc., 33(1):16-24 (2000).
Written Opinion for PCT/US2013/038186, 7 pages (dated Sep. 27, 2013).
Zapata, G. et al., Engineering linear F(ab')$_2$ fragments for efficient production in *Escherichia coli* and enhanced antiproliferative activity, Protein Engineering, 8(10):1057-1062 (1995).
Zhang, Y-Q et al., Formation of silk fibroin nanoparticles in water-miscible organic solvent and their characterization, Journal of Nanoparticle Research, 9:885-900 (2007).
Zheng, R. et al., Lubrication Properties of Phospholipid Liposome Coated Silk Microspheres, Particle and Particle Systems Characterization, 30(2):133-137 (2013).
Extended European Search Report for EP13780602.2, 7 pages (dated Oct. 26, 2015).
Verberne, G. et al., Liposome as potential biolubricant additives for wear reduction in human synovial joints, Wear, 268(7-8):1037-1042 (2010).

\* cited by examiner

SILK MICROSPHERES AND METHODS FOR SURFACE LUBRICATION

CROSS REFERENCE TO RELATED APPLICATIONS

This application claims the benefit under 35 U.S.C. § 119(e) of U.S. Provisional Application Nos. 61/638,294 filed Apr. 25, 2012 and 61/778,794 filed Mar. 13, 2013, the contents of which are incorporated herein by reference in their entireties.

GOVERNMENT SUPPORT

This invention was made with government support under grants EB002520 awarded by the National Institutes of Health and FA9550-10-1-0172 awarded by the United States Air Force. The government has certain rights in the invention.

TECHNICAL FIELD

Provided herein relates to compositions and methods for surface lubrication. In some embodiments, the compositions and methods can be used for joint lubrication, e.g., for treatment of joint disorders.

BACKGROUND OF THE DISCLOSURE

Arthritis is a joint disorder that is caused by inflammation of one or more joints. It has been estimated that the total cost of the arthritis bill for the United States is over $50 billion dollars annually [Corti, M. C. et al. Exp. Res. (2003)15: 359-363]. Among many types of arthritis (e.g., over 100 identified), osteoarthritis (OA) is the most common type with a prevalence exceeding 20 million in the United States. Id. The cause of OA is generally related to wear and tear of the cartilage on the surfaces, while another common type of arthritis, rheumatoid arthritis, is typically caused by the inflammation resulting from an overactive immune system. The treatment of arthritis is dependent on the precise type of arthritis.

Current treatment of OA mainly focuses on joint mobilization, which is enabled by avoiding overloading as well as control of pain and inflammation using medications administered systemically or intra-articularly [Grainger, R. and Cicuttini, F. M. Med. J. Aust. (2004)180:232-236]. Lubricant molecules that separate opposing surfaces can reduce friction under the pressure and, therefore, supplementation of biolubricants in synovial fluid (SF) is a reasonable option for treatment of OA [Abate, M. and Pelotti, P., J. Med. Sci. (2008)113:261-278].

Several different substances have been proposed as the native boundary biolubricants. Hyaluronic acid (HA) and the glycoprotein lubricin are the two main components in SF. HA is a polymer of D-glucuronic acid and D-N-acetyl-glucosamine, which degrades under inflammatory conditions such as in OA. Clinical application of HA (so called viscosupplementation), however, did not demonstrate the efficacy of HA in treating OA [Benz, M. and Chen, N. J. Biomed. Mater. Res., Part A (2004) 71:6-15]. On the other hand, lubricin is generally composed of ~44% proteins, ~45% carbohydrates, and ~11% surface active phospholipids (SAPL), of which ~41% are phosphatidylcholines (PCs), ~27% phosphatidylethanolamines (PEs), and ~32% sphingomyelins [Swann, D. A. et al. Arthritis Rheum. (1981) 24:22-30; Swann, D. A. and Mintz, G. Biochem. J. (1979) 179:465-471; Swann, D. A. et al. J. Biol. Chem. (1981) 256:5921-5925; Schwarz, I. M. and Hills, B. A. Br. J. Rheumatol. (1998) 37:21-26; Sarma, A. V. et al. J. Orthoped. Res. (2001)19:671-676]. The SAPL in SF has been previously reported to facilitate low friction in articulating cartilage. For example, injection of the SAPL 1,2-dipalmitoyl-phosphtidylcholine (DPPC) into human OA joints that are SAPL deficient was reported to result in mobility improvement lasting up to 14 weeks without major side effects [Vecchio, P. and Thomas, R.; Hills, B. A. Rheumatology (1999) 38:1020-1021; Oloyede, A. et al. Clin. Biomech. (2004) 19:534-542]. A previous report on globular lipid vesicles localized in the thick upper surface layer of healthy cartilage indicates their role in lubrication [Watanabe, M. et al. Med. Electron Microsc. (2000) 33; 16-24]. DPPC liposomes combined with high molecular weight HA (~2000 kDa) had shown better lubricating ability than HA alone in animal models [Kawano, T. et al. Arthritis Rheum. (2003) 48:1923-1929]. Recently, size and composition effect of different liposomes on joint lubrication has been compared using an ex-vivo model [Sivan, S. et al. Langmuir (2010) 26:1107-1116]. Although the role of SAPL in joint lubrication has been reported, clinical applications of these SAPL molecules still remain challenging. This is partly because SAPL has low molecular weight and does not have stable and robust material properties to sustain the therapeutic effect. Therefore, there is still a need to develop a clinically viable and effective formulation for treatment of joint disorders such as OA.

SUMMARY

Clinical use of phospholipids alone as a biolubricant is not reliable or effective, partly because the low molecular weight phospholipids do not have stable or robust material properties to sustain the therapeutic effect. The inventors have discovered inter alia lubrication properties of an aqueous phospholipid-coated silk microsphere suspension, which can provide a low friction coefficient, minimize surface wear and/or avoid degradation even over relatively prolonged cycling conditions. In particular, in some embodiments, silk microspheres prepared via either 1,2-dioleoyl-sn-glycero-3-phosphocholine (DOPC) template or polyvinyl alcohol (PVA) phase separation methods were coated with DOPC. The coating was achieved either during the microsphere preparation for the DOPC template method or post preparation for the PVA-based method. Both types of DOPC-coated microspheres showed effective lubrication effects in in vitro friction tests. The friction coefficient reduced from about 0.2-0.3 for silk microspheres alone to about 0.03-0.04 for DOPC-coated microspheres, which is even lower than that of DOPC liposomes alone (~0.055). Compared to the DOPC liposomes alone, the DOPC-coated silk microspheres effectively prevented the contacted surfaces from wearing during the tests. Accordingly, provided herein are compositions and methods for lubrication of one or more surfaces using lipid-coated silk microspheres. In some embodiments, the compositions and methods described herein can be used to lubricate one or more non-biological surfaces. In other embodiments, the compositions and methods described herein can be used to lubricate one or more biological surfaces in vivo, e.g., in a mammalian subject to lubricate joint surfaces, e.g., for treatment of a joint disorder such as arthritis.

One aspect provided herein relates to compositions comprising at least one lipid-coated silk microsphere. In some embodiments, the compositions described herein can be used as a lubricant composition anywhere, e.g., to reduce friction between two surfaces of a machine or a device, or between two surfaces of a joint in a mammalian subject.

For example, in some embodiments, the lipid-coated silk microsphere can yield a coefficient of friction (e.g., a coefficient of static friction) of less than 0.2 or lower, as determined by a friction test against a silica surface. In some embodiments, the lipid-coated silk microsphere can yield a coefficient of friction (e.g., a coefficient of static friction) of less than 0.1 or lower (e.g., about 0.099, about 0.09, about 0.08, about 0.07, about 0.06, about 0.05, about 0.04, about 0.03, about 0.02, about 0.01 or lower, as determined by a friction test against a silica surface.

The coefficient of friction for motion between the lipid-coated silk microsphere and a surface generally depends on system variables, e.g., but not limited to, materials of the opposing surfaces, temperature, velocity, atmosphere, and/or geometric and topographical properties of the interface between the materials. Accordingly, in some embodiments, the lipid-coated silk microsphere can have a substantially smooth surface morphology, e.g., to achieve a low friction coefficient of less than 0.2 or lower, as determined by a friction test against a silica surface.

While the lipid-coated silk microsphere can be in any shape or form, including, e.g., spheres, rods, prisms, discs, polyhedrons, in some embodiments, the lipid-coated silk microsphere can be substantially spherical, e.g., to achieve a low friction coefficient of less than 0.2 or lower, as determined by a friction test against a silica surface.

The size of the lipid-coated silk microsphere can vary with a number of factors, e.g., but not limited to, condition of an application site (e.g., gap dimension between two surfaces), fabrication methods, and/or lipid coating thickness. Accordingly, the lipid-coated silk microsphere can have a width dimension in nanometers or in micrometers, e.g., ranging from about 10 nm to about 100 µm The inventors have discovered that, in some embodiments, larger lipid-coated silk microspheres were more effective than sub-micron particles in facilitating lubrication. Without wishing to be bound by theory, the larger lipid-coated silk microspheres can facilitate surface lubrication through a mechanism of rolling friction between two surfaces. Thus, in some embodiments, the lipid-coated silk microsphere can range from about 1 µm to about 100 µm, or from about 1 µm to about 75 µm, or from about 2 µm to about 50 µm, or from about 3 µm to about 25 µm. In some embodiments, the lipid-coated silk microsphere can have a width dimension of at least about 3 µm or higher.

Without wishing to be bound by theory, a silk microsphere can act as a cushion to provide support for lipid components, thus sustaining the lubrication property of the lipid components under cyclic shear loading. Accordingly, in contrast to lipid liposomes alone, a combination of the lipid components and a mechanically robust silk fibroin material can permit the resulting lipid-coated silk microsphere to be more resistant to degradation under cyclic shear loading.

A lipid-coated silk microsphere is a silk microsphere comprising on its surface at least one lipid component. The lipid component can form a unilamellar or multilamellar structure on the surface of the silk microsphere. In some embodiments, the silk microsphere can further comprise lipid component embedded in the silk microsphere. Any art-recognized naturally-occurring or synthetic lipid component can generally be used to form a lipid coating of the lipid-coated silk microsphere. For example, any lipid component that can form a liposome in an aqueous solution can be used to form a lipid coating of the lipid-coated silk microsphere. In some embodiments, the lipid component can comprise one or more phospholipids. Non-limiting examples of phospholipids include, but are not limited to, phosphatidylcholine; phosphatidylethanolamine; phosphatidylserine; phosphatidylinositol; phosphatidic acid; palmitoyloleoyl phosphatidylcholine; lysophosphatidylcholine; lysophosphatidylethanolamine; dipalmitoylphosphatidylcholine; dioleoylphosphatidylcholine; distearoylphosphatidylcholine; dilinoleoylphosphatidylcholine; 1,2-dioleoyl-sn-glycero-3-phosphocholine (DOPC); 1,2-dioleoyl-sn-glycero-3-phosphoethanolamine (DOPE); 1,2-dilauroyl-sn-glycero-3-phosphocholine (DLPC); 1,2-dimyristoyl-sn-glycero-3-phosphocholine (DMPC); 1,2-dipalmitoylphosphtidylcholine (DPPC), and any combinations thereof. In one embodiment, said at least one lipid component comprises 1,2-dioleoyl-sn-glycero-3-phosphocholine (DOPC).

The lipid-coated silk microsphere can have lipid component(s) in any amount that is sufficient to yield a desirable coefficient of friction. In general, the coefficient of friction of a lipid-coated silk microsphere against a surface decreases as the concentration of the lipid component in the lipid-coated silk microsphere increases. In some embodiments, the amount of the lipid component present in the silk microsphere (e.g., on its surface) can range from about 0.01 wt % to about 10 wt %, or about 0.05 wt % to about 5 wt %.

In some embodiments, the lipid-coated silk microsphere and/or the composition can further comprise an additive or active agent. The additive or active agent can be present on the lipid coating, the silk microsphere, or a combination thereof, or can be independently present in the composition described herein. Exemplary additives or active agents that can be included in the lipid-coated silk microsphere and/or the composition include, without limitations, biopolymers, nanoparticles (e.g., gold nanoparticles), proteins, peptides, nucleic acids (e.g., DNA, RNA, siRNA, modRNA), nucleic acid analogs, nucleotides, oligonucleotides, peptide nucleic acids (PNA), aptamers, antibodies or fragments or portions thereof (e.g., paratopes or complementarity-determining regions), antigens or epitopes, hormones, hormone antagonists, growth factors or recombinant growth factors and fragments and variants thereof, cytokines, enzymes, small molecules, antibiotics or antimicrobial compounds, toxins, therapeutic agents and prodrugs, small molecules, cells, naturally-occurring or synthetic lubricants (e.g., but not limited to, hyaluronic acid, lubricin), and any combinations thereof.

In some embodiments, the silk microsphere can comprise a porous structure.

As discussed above, a suspension of the lipid-coated silk microspheres described herein possesses lubrication properties. Accordingly, another aspect described herein relates to methods of reducing friction between two surfaces. The method comprises placing between a first surface and a second surface a composition comprising at least one lipid-coated silk microsphere described herein. In some embodiments, the placement of the composition described herein can reduce friction between the first surface and the second surface by at least about 10% or more, as compared to the friction between the two surfaces without the composition. In some embodiments, the method can further comprise shearing the composition between the first surface and the second surface.

In addition to lubrication properties, the inventors have also discovered anti-wearing effect of the lipid-coated silk microspheres described herein (e.g., DOPC-coated silk microspheres). For example, in a friction test, the wear pattern formed after shearing a glass probe against a silicon surface under cyclic shear loading was less prevalent in the presence of the lipid-coated silk microspheres (e.g., DOPC-coated silk microspheres) than in the presence of the lipid liposomes alone as the lubricant. Thus, during a shear, the lipid-coated silk microsphere within the composition can reduce, e.g., by at least about 10% or more, wearing of either one or both of the first surface and the second surface, as compared to when a lipid-coated non-silk microsphere is used.

In some embodiments, the first surface and the second surface can be present in a mammalian subject. For example, the first surface and the second surface can comprise opposing surfaces of a joint. Thus, a method of treating a joint disorder, e.g., arthritis, in a subject is also provided herein. The method comprises placing between two joint surfaces one or more embodiments of the composition described herein, thereby reducing friction between the two joint surfaces.

The lipid-coated silk microspheres in the compositions described herein can be prepared by any methods known in the art. For example, a lipid coating can be formed on the surface of the silk microspheres during the microsphere preparation and/or post-preparation of the silk microspheres. In some embodiments, a lipid-coated silk microsphere can be produced by a method using a lipid composition to form a template, the method comprising: (a) sonicating a mixture comprising a silk fibroin solution and a lipid composition, thereby forming a suspension comprising lipid-coated silk microspheres; and (b) lyophilizing at least a portion of the lipid-coated silk microspheres.

The concentration of the lipid composition in the mixture can vary, e.g., with a desired amount of lipid components formed on the coating. In some embodiments, the concentration of the lipid composition in the mixture can vary from about 5 wt % to about 50 wt %, or about 10 wt % to about 30 wt %. In one embodiment, the concentration of the lipid composition in the mixture can be about 20 wt %.

In alternative embodiments, a lipid-coated silk microsphere can be produced by a method based on PVA phase separation, the method comprising: (a) sonicating a mixture comprising a silk fibroin solution and a polyvinyl alcohol (PVA) solution; (b) lyophilizing the mixture; (c) dissolving the lyophilized mixture in an aqueous solution; (d) removing at least a portion of the PVA, thereby forming a silk microsphere; and (e) sonicating the silk microsphere with a hydrated lipid composition, thereby forming a lipid-coated silk microsphere.

The final concentration of the hydrated lipid composition in the mixture can vary, e.g., with a desired amount of lipid components formed on the coating. In some embodiments, the final concentration of the hydrated lipid composition in the mixture can range from about 0.05 wt % to about 10 wt %, or from about 0.1 wt % to about 2 wt %.

In some embodiments, the final concentration of the PVA solution in the mixture can vary from about 0.5 wt % to about 20 wt %, or from about 1 wt % to about 10 wt %.

Depending on the concentrations of the silk fibroin solution and the polyvinyl alcohol (PVA) solution, the volume ratio of the silk fibroin solution to the PVA solution can vary accordingly, provided that the final concentrations of the silk fibroin solution and the PVA solution are satisfied as described above. In some embodiments, the volume ratio of the silk fibroin solution to the PVA solution is about 1:1 to about 1:10, or about 1:2 to about 1:5. In one embodiment, the volume ratio of the silk fibroin solution to the PVA solution is about 1:4.

In some embodiments of the different methods for making a lipid-coated silk microsphere (e.g., the lipid template-based and PVA phase separation-based methods), the method can further comprise separating the smaller-sized lipid-coated silk microspheres from the larger-sized lipid-coated microspheres. For example, for the lipid template-based methods, the method can further comprise separating the smaller-sized lipid-coated silk microspheres form the larger-sized lipid-coated microspheres prior to lyophilization. For the PVA phase separation-based methods, the method can further comprise separating the smaller-sized lipid-coated silk microspheres from the larger-sized lipid-coated microspheres after the silk microsphere is formed, e.g., prior to coating the silk microsphere with a lipid composition. Methods for separating particles based on sizes are known in the art, including, e.g., but not limited to, sieving, filtration, and/or centrifugation, and can be used herein to separate smaller-sized lipid-coated silk microspheres from the larger-sized lipid-coated microspheres. In one embodiment, the smaller-sized lipid-coated silk microspheres can be separated from the larger-sized lipid-coated silk microspheres by centrifugation.

The silk fibroin solution can have any concentration that is suitable to form silk microspheres that can act as lubricants and sustain cyclic shear loading. In some embodiments, the silk fibroin solution can have a concentration of about 1 wt % to about 30 wt %, or a concentration of about 3 wt % to about 15 wt %.

As noted above, one or more naturally-occurring or synthetic lipid components can be used to form a lipid coating on the silk microspheres described herein. For example, one or more naturally-occurring or synthetic lipid components that can form liposomes can be used to form a lipid coating on the silk microspheres described herein. In some embodiments, the lipid composition can comprise one or more phospholipids. Examples of said one or more phospholipids include, but are not limited to, phosphatidylcholine; phosphatidylethanolamine; phosphatidylserine; phosphatidylinositol; phosphatidic acid; palmitoyloleoyl phosphatidylcholine; lysophosphatidylcholine; lysophosphatidylethanolamine; dipalmitoylphosphatidylcholine; dioleoylphosphatidylcholine; distearoylphosphatidylcholine; dilinoleoylphosphatidylcholine; 1,2-dioleoyl-sn-glycero-3-phosphocholine (DOPC); 1,2-dioleoyl-sn-glycero-3-phosphoethanolamine (DOPE); 1,2-dilauroyl-sn-glycero-3-phosphocholine (DLPC); 1,2-dimyristoyl-sn-glycero-3-phosphocholine (DMPC); and any combinations thereof.

A lipid-coated silk microsphere produced by one or more embodiments of the lipid template-based method as well as the PVA phase separation-based method are also provided herein. These lipid-coated silk microspheres can be used as a lubricant to reduce friction between any two surfaces and/or reduce wear over time. In some embodiments, the lipid-coated silk microspheres can be used as a lubricant to reduce friction between any two joint surfaces (e.g., surfaces comprising bone and/or cartilage).

BRIEF DESCRIPTION OF THE DRAWINGS

FIG. 2A shows DOPC and silk mixture prior to sonication (sample LS in Table 1). The sample contained vesicles with inhomogeneous sizes of 1-20 μm. FIG. 2B shows the sample from FIG. 2A after sonication. The vesicles were homogenized to a size range of 1-10 μm. FIG. 2C shows supernatant from the centrifugation of the sample from FIG. 2B, which was dominated by microspheres with a narrower size range of 1-2 μm. FIG. 2D shows resuspended pellet from the centrifugation of the sample from FIG. 2B, which was dominated by microspheres with larger sizes (5-10 μm).

FIG. 3A shows the size distribution of particles present in the supernatant collected from the centrifugation, which was dominated by nanoparticles. FIG. 3B shows the size distribution of particles present in the suspension of the pellet after centrifugation, which was dominated by microparticles.

FIGS. 6A-6B show cushioning effect of silk microspheres prepared using PVA phase separation method and further coated with DOPC (1.25 wt %) in friction tests. FIG. 6A is a plot corresponding to DOPC liposome alone. FIG. 6B is a plot corresponding to DOPC coated silk microspheres.

FIG. 7A shows that the DOPC liposomes left friction marks on the silicon surface after the cyclic shear loading, while FIG. 7B shows no wearing effects on the silicon surface in the presence of the DOPC-coated silk microspheres.

FIG. 13A shows that the DOPC liposomes left friction marks on the silicon surface after the cyclic shear loading, while FIG. 13B shows little or no wearing effects on the silicon surface in the presence of the DOPC-coated silk microspheres.

FIG. 18A is a low-resolution image of DOPC-coated silk microspheres. FIGS. 18B-18H show optical sections collected at different levels perpendicular to the optical axis (the z-axis, and the step size in the Z-direction is 2 μm). FIGS. 18I-18J are cryo-SEM images showing small irregular cross-sections of DOPC-coated silk microspheres. Scale bar: (FIGS. 18A-18H) 20 μm; (FIGS. 18I-18J) 10 μm.

DETAILED DESCRIPTION OF THE INVENTION

Figure 1:
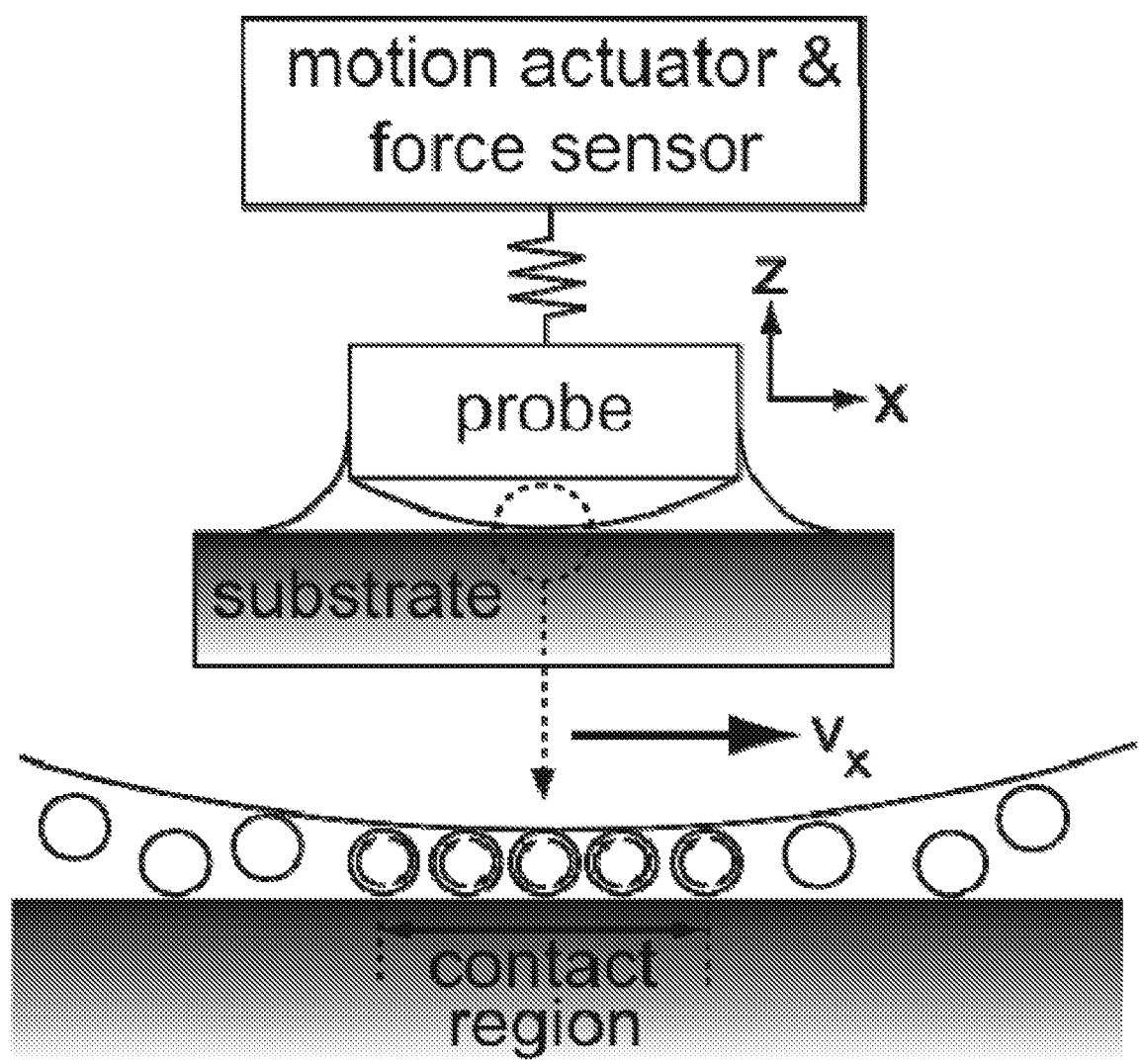
FIG. 1 is a schematic representation of an exemplary friction testing setup.

Joint lubrication is a new therapeutic option for osteoarthritis (OA), by which a biomaterial is injected into damaged joints to reduce the friction between cartilage surfaces, thus relieving the symptoms such as pain and inflammation. A natural polymer material, hyaluronic acid, has been previously used for this purpose but the effect was not satisfying. Phospholipids are the major surface-active component in synovial fluid (SF) that is beneficial to joint lubrication. However, clinical use of phospholipids alone as a biolubricant is not reliable or effective. Provided herein are compositions and methods for lubrication of one or more surfaces. In some embodiments, the compositions and methods described herein can be used to lubricate one or more non-biological surfaces. In other embodiments, the compositions and methods described herein can be used to lubricate one or more biological surfaces in vivo, e.g., in a mammalian subject for joint lubrication.

The inventors have discovered inter alia lubrication properties of phospholipid-coated silk microspheres. In particular, silk microspheres prepared via either 1,2-Dioleoyl-sn-glycero-3-phosphocholine (DOPC) template or polyvinyl alcohol (PVA) phase separation methods were coated with DOPC. The coating was achieved either during the microsphere preparation for the DOPC template method or post preparation for the PVA-based method. Both DOPC-coated microspheres showed effective lubrication effects in in vitro friction tests. The friction coefficient reduced from about 0.2-0.3 for silk microspheres alone to about 0.03-0.04 for DOPC-coated microspheres, which is even lower than that of DOPC liposomes alone (~0.055). Further, the inventors have shown that, in some embodiments, larger microspheres (1-5 µm) were more effective than sub-micron particles in facilitating lubrication. Compared to the DOPC liposomes alone, the DOPC-coated silk microspheres effectively prevented the contacted surfaces from wearing during the tests. Accordingly, formulations of phospholipid-coated silk microspheres provide effective lubricant compositions. In some embodiments, the formulation of phospholipid-coated silk microspheres can provide an effective treatment of joint disorders such as arthritis.

Compositions Comprising a Lipid-Coated Silk Microsphere

One aspect provided herein relates to compositions comprising at least one or a plurality of lipid-coated silk microsphere. The term "lipid-coated silk microsphere" as used herein refers to a silk fibroin-based microsphere comprising on its surface a lipid-based coating, wherein the lipid-based coating comprises at least one lipid component or any combinations of the lipid components described herein. In some embodiments, the lipid-based coating can further comprise at least one or more additives or active agents described herein. The lipid component(s) can form a unilamellar (e.g., a single lamella layer) or multilamellar (e.g., two or more lamellae layers) structure or vesicle surrounding or encapsulating the silk fibroin-based microsphere. Stated another way, a lipid-coated silk microsphere can be a lipid-based unilamellar (e.g., a single lamella layer) or multilamellar (e.g., two or more lamellae layers) vesicle with a silk fibroin-based microsphere being encapsulated therein. In some embodiments, the silk fibroin-based microsphere can further comprise one or more lipid components embedded within the silk fibroin-based microsphere.

As used herein, the term "silk fibroin-based microsphere" refer to a microsphere in which silk fibroin constitutes at least about 30% of the total composition, including at least about 40%, at least about 50%, at least about 60%, at least about 70%, at least about 80%, at least about 90%, at least about 95%, up to and including 100% or any percentages between about 30% and about 100%, of the total composition. In certain embodiments, the silk fibroin-based microsphere can be substantially formed from silk fibroin. In various embodiments, the silk fibroin-based microsphere can be substantially formed from silk fibroin comprising at least one additive (e.g., but not limited to, an active agent).

In some embodiments, the compositions described herein can be used as a lubricant composition anywhere, e.g., to reduce friction between two surfaces of a machine or a device, or between two surfaces of a joint in a mammalian subject. Accordingly, in some embodiments, the lipid-coated silk microsphere can yield a coefficient of friction (e.g., a coefficient of static friction or a coefficient of kinetic friction) of less than 0.2 or lower, as determined by a friction test against a silica surface. In some embodiments, the lipid-coated silk microsphere can yield a coefficient of friction (e.g., a coefficient of static friction or a coefficient of kinetic friction) of less than 0.1 or lower (e.g., about 0.099, about 0.09, about 0.08, about 0.07, about 0.06, about 0.05, about 0.04, about 0.03, about 0.02, about 0.01 or lower, as determined by a friction test against a silica surface. It is readily understood by one of skill in the art that the coefficient of friction of a lipid-coated silk microsphere against a silica surface will be different from that of the same lipid-coated silk microsphere against a different surface (e.g., but not limited to, different material, surface morphology and/or geometric properties).

In some embodiments, the lipid-coated silk microsphere can yield a coefficient of friction (e.g., a coefficient of static friction or a coefficient of kinetic friction) that is lower than that of a lipid-coated non-silk microsphere, or that of a liposome formed by the same lipid components present on the coating of the lipid-coated silk microsphere. For example, the lipid-coated silk microsphere can yield a coefficient of friction (e.g., a coefficient of static friction or a coefficient of kinetic friction) that is at least about 10%, including, e.g., at least about 20%, at least about 30%, at least about 40%, at least about 50%, at least about 60%, at least about 70%, at least about 80%, at least about 90% or more, lower than that of a lipid-coated non-silk microsphere, or that of a liposome formed by the same lipid components present on the coating of the lipid-coated silk microsphere.

Figure 6A:
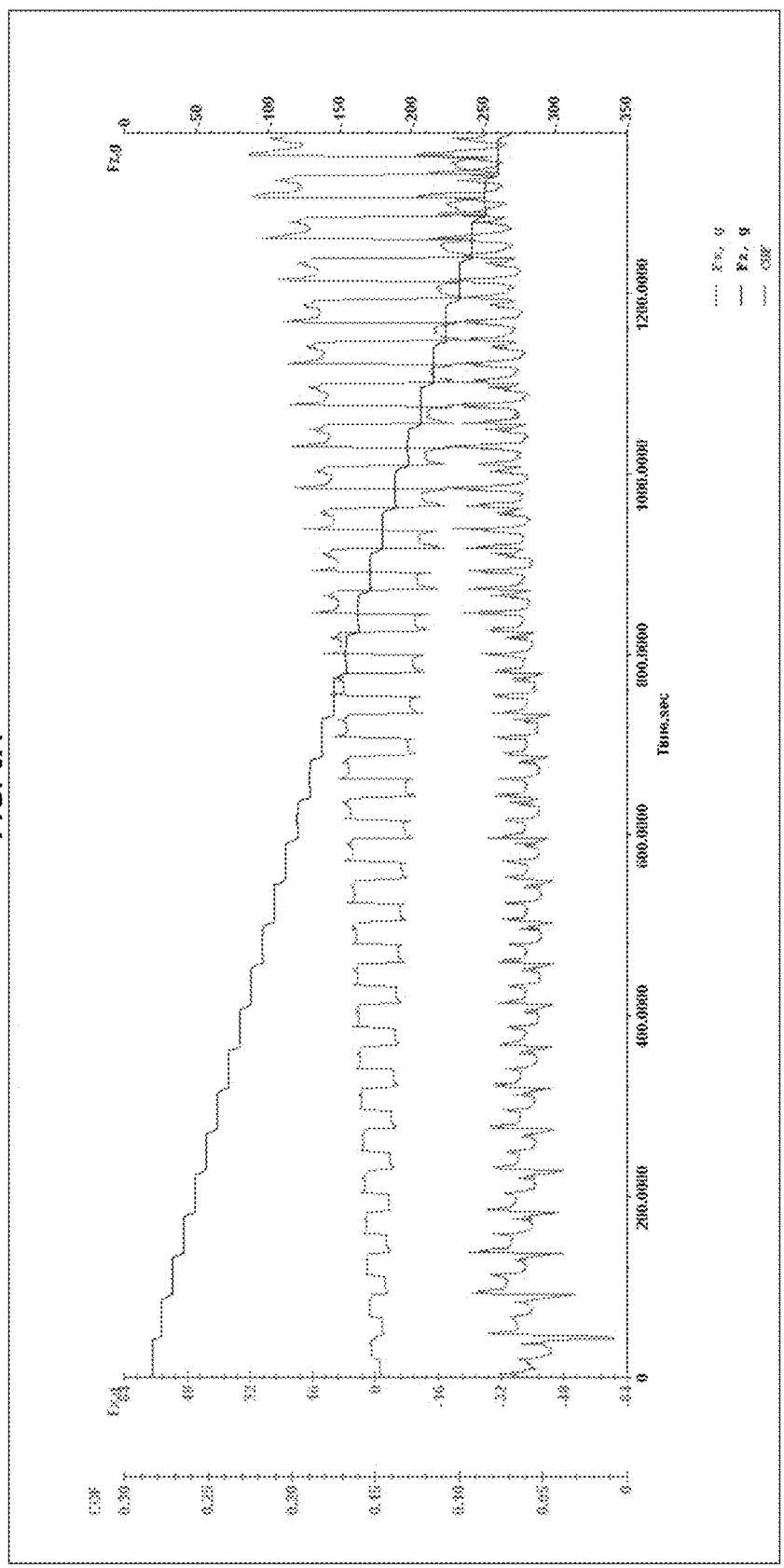
FIGS. 6A-6B are plots of typical friction force Fx, applied load Fz and coefficient friction (COF) trace versus time while shearing a spherical glass probe against a silicon surface at a load of about 0.196N (20 g) to about 24.5 N (250 g) in the presence of DOPC liposome (FIG. 6A) as the lubricant, or DOPC lipid-coated silk microspheres suspension (FIG. 6B) as the lubricant.
Figure 6A:
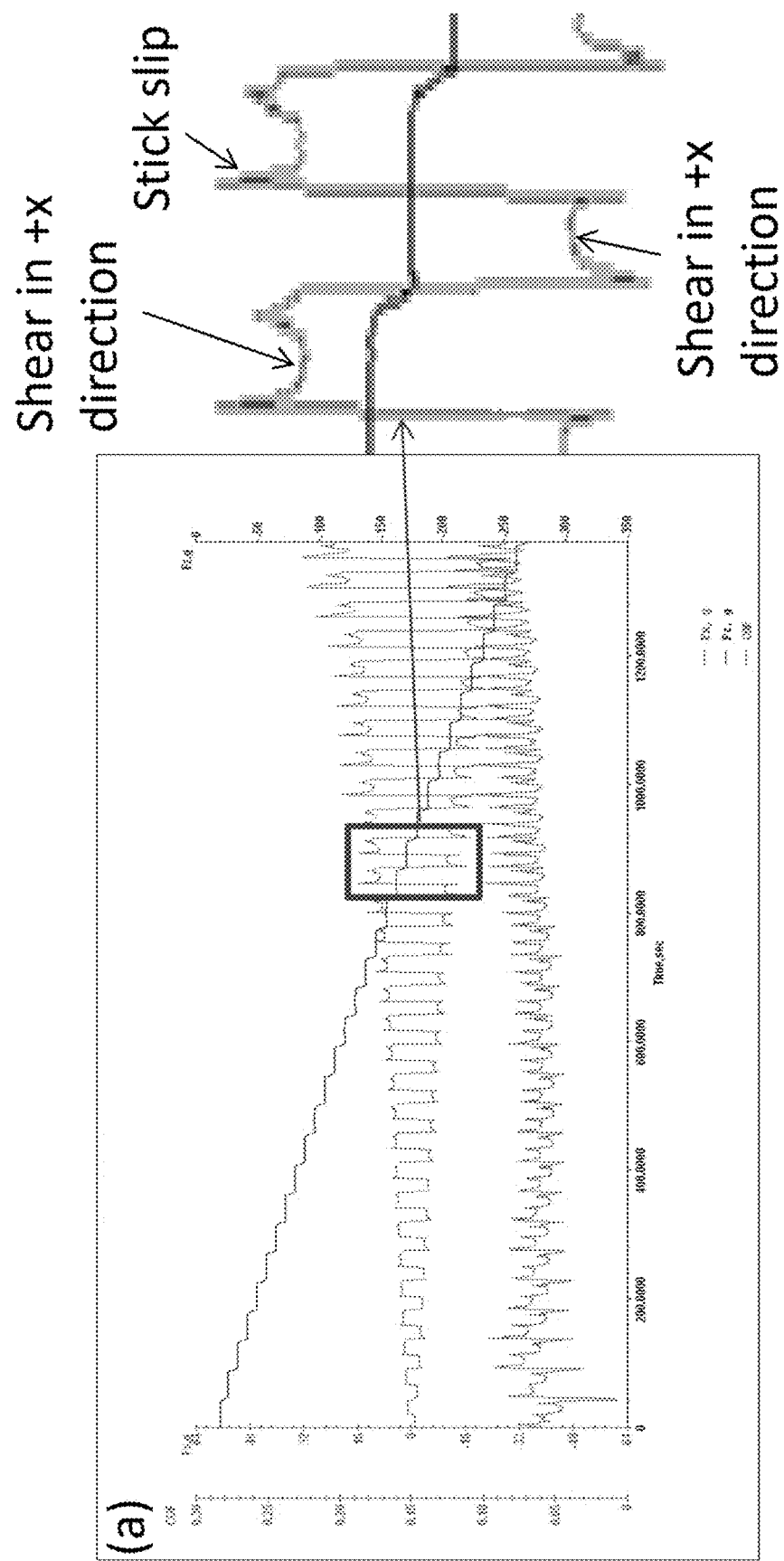
Figure 6B:
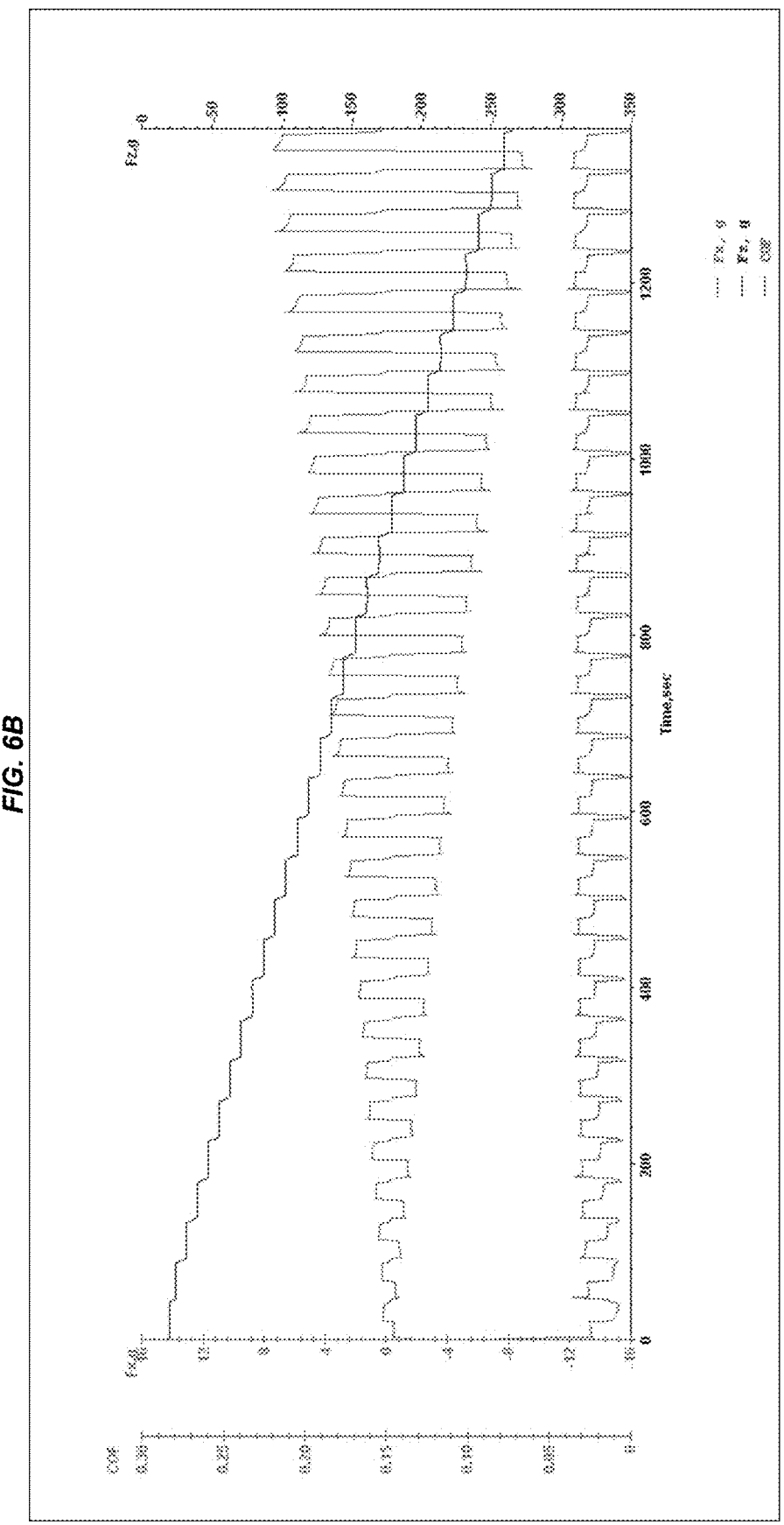
Figure 6B:
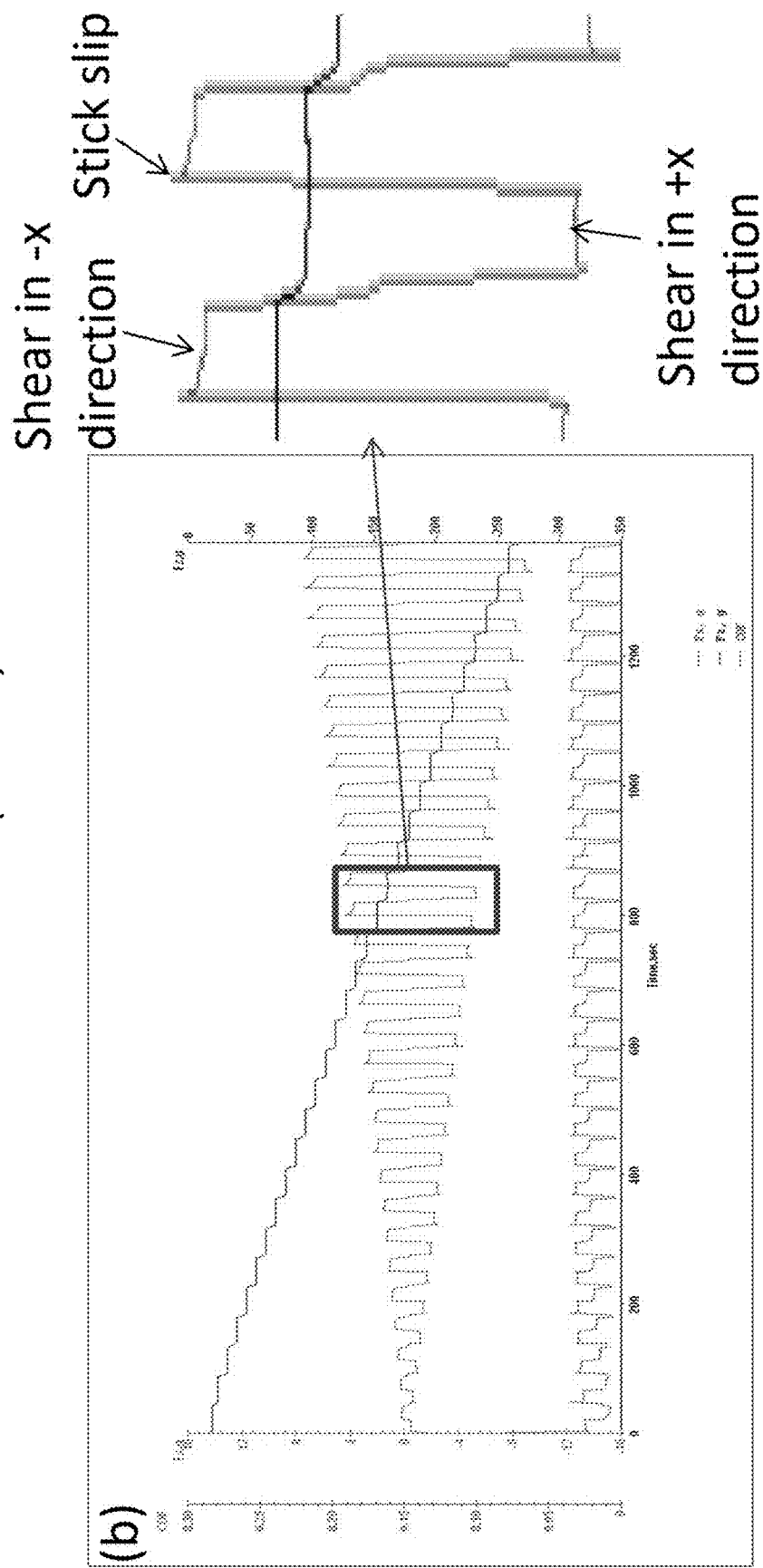

Various methods for determination of a coefficient of friction of a material are known in the art, for example, but not limited to atomic force microscopy, which can be used to determine coefficient of friction of a lipid-coated silk microsphere. For example, a universal materials tester (UMT) can be used to measure the friction force and lubrication properties between two surfaces, e.g., a spherical glass tip and flat silica wafer (FIG. 1). The two surfaces (e.g., glass tip and silica wafer) can be immersed in a bath containing lipid-coated silk microsphere suspension, and one of the surfaces (e.g., glass tip) can be pulled horizontally at a controlled velocity while the friction force, F, between the two surfaces is continuously measured. The friction coefficient $\mu=F/N$ is calculated and plotted as a function of pulling time (seconds), e.g., as shown in FIGS. 6A-6B. The static friction coefficient can be obtained from the maximum value of the plot.

The coefficient of friction for the lipid-coated silk microsphere against a surface generally depends on system variables, e.g., but not limited to, materials of the opposing surfaces, temperature, velocity, atmosphere, and/or geometric and topographical properties of the interface between the materials. Accordingly, in some embodiments, the lipid-coated silk microsphere can be adapted to have a substantially smooth surface morphology, e.g., to achieve a low friction coefficient of less than 0.2 or lower, as determined by a friction test against a silica surface. For example, the smoothness of the surface morphology of a lipid-based silk microsphere described herein can be controlled, in part, by, for example, the concentration of a lipid composition, thickness and/or composition of the lipid-based coating, and/or the microsphere fabrication process.

While the lipid-coated silk microsphere can be in any shape or form, including, e.g., spheres, rods, prisms, shells, discs, polyhedrons, in some embodiments, the lipid-coated silk microsphere can be substantially spherical, e.g., to achieve a low friction coefficient of less than 0.2 or lower, as determined by a friction test against a silica surface. By the term "substantially spherical" is meant that the ratio of the lengths of the longest to the shortest perpendicular axes of the particle cross section is less than or equal to about 1.5. Substantially spherical does not require a line of symmetry.

Further, the lipid-based silk microsphere can have surface texturing, such as lines or indentations or protuberances that are small in scale when compared to the overall size of the microsphere and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1.

The size of the lipid-coated silk microsphere can vary with a number of factors, e.g., but not limited to, condition of an application site (e.g., gap dimension between two surfaces), fabrication methods, and/or lipid coating thickness. Accordingly, the lipid-coated silk microsphere can have a width dimension in nanometers or in micrometers, e.g., ranging from about 10 nm to about 100 μm The inventors have discovered that, in some embodiments, larger lipid-coated silk microspheres were more effective than sub-micron particles in facilitating lubrication. Without wishing to be bound by theory, the larger lipid-coated silk microspheres can facilitate surface lubrication through a mechanism of rolling friction between two surfaces. Thus, in some embodiments, the lipid-coated silk microsphere can range from about 1 μm to about 100 μm, or from about 1 μm to about 75 μm, or from about 2 μm to about 50 μm, or from about 3 μm to about 25 μm. In some embodiments, the lipid-coated silk microsphere can have a width dimension of at least about 3 μm or higher, including, e.g., at least about 4 μm, at least about 5 μm, at least about 6 μm, at least about 7 μm, at least about 8 μm, at least about 9 μm, at least about 10 μm, at least about 15 μm, at least about 20 μm, at least about 25 μm, at least about 30 μm or more. It will be understood by one of ordinary skill in the art that microspheres usually exhibit a distribution of microsphere sizes around the indicated "size." Unless otherwise stated, the term "size" as used herein refers to the mode of a size distribution of microspheres, i.e., the value that occurs most frequently in the size distribution. Methods for measuring the microsphere size are known to a skilled artisan, e.g., by dynamic light scattering (such as photo correlation spectroscopy, laser diffraction, low-angle laser light scattering (LALLS), and medium-angle laser light scattering (MALLS)), light obscuration methods (such as Coulter analysis method), optical microscopy (e.g., at a phase contrast mode), a particle analyzer, or other techniques (such as rheology, and light or electron microscopy).

Without wishing to be bound by theory, a silk microsphere can act as a cushion to provide support for lipid components, thus sustaining the lubrication property of the lipid components under cyclic shear loading. Accordingly, a combination of the lipid components and a mechanically robust silk fibroin material can permit the resulting lipid-coated silk microsphere to be more resistant to degradation under cyclic shear loading (e.g., cyclic physiological shear loading level), as compared to lipid liposomes alone. For example, physiological pressures in joints are typically between about 0.08 MPa and about 2.4 MPa (Sivan et al., Langmuir, 2010, 26 (2), 1107-1116). The phrase "resistant to degradation" as used herein refers to the ability of lipid-based silk microspheres to resist erosion or degradation that may occur, for example, by enzymatic, chemical or physical processes, for a period of time. In some embodiments, the lipid-coated silk microsphere can be resistant to degradation under cyclic shear loading (e.g., cyclic physiological shear loading level) for a longer period of time than that of the lipid liposomes alone, e.g., by at least about 1 week longer, at least about 2 weeks longer, at least about 3 weeks longer, at least about 1 month longer, at least about 2 months longer, at least about 3 months longer, at least about 6 months longer, at least about 9 months longer, at least about 12 months longer, at least about 2 years longer. In some embodiments, the lipid-coated silk microsphere can stay in-between two surfaces (e.g., of a machine or in vivo) for a significantly long amount of time, or even permanently.

In some embodiments, the lipid-coated silk microsphere can withstand a cyclic shear loading force of at least about 0.49 N or higher, for at least about 100 cycles or more, including, e.g., at least about 200 cycles, at least about 300 cycles, at least about 400 cycles, at least about 500 cycles or more, before it degrades. It will be readily understood to one of skill in the art that the lipid-coated silk microsphere can withstand much longer before it degrades, if the cyclic shear loading force is smaller.

In some embodiments, the lipid-coated silk microsphere can withstand a loading pressure (e.g., a cyclic pressure) of at least about 60 MPa or higher, for at least about 100 cycles or more, including, e.g., at least about 200 cycles, at least about 300 cycles, at least about 400 cycles, at least about 500 cycles or more, before it degrades. It will be readily understood to one of skill in the art that the lipid-coated silk microsphere can withstand much longer before it degrades, if the loading pressure is smaller.

In some embodiments, degree of degradation of lipid-coated silk microspheres described herein can be reflected by the lubrication properties of the lipid-coated silk microspheres, e.g., coefficient of friction. For example, the lipid-coated silk microspheres being able to maintain substantially the same lubrication properties after a cyclic shear loading (e.g., a shear loading of about 0.49 N for about 500 cycles) can be indicative of no significant degradation of the lipid-coated silk microspheres. Accordingly, in some embodiments, the lipid-coated silk microsphere can maintain its lubrication properties (e.g., indicated by coefficient of friction) after subjected to a cyclic shear loading force of at least about 0.49 N or higher, for at least about 100 cycles or more, including, e.g., at least about 200 cycles, at least about 300 cycles, at least about 400 cycles, at least about 500 cycles or more. It will be readily understood to one of skill in the art that the lipid-coated silk microsphere can maintain its lubrication properties (e.g., indicated by coefficient of friction) much longer, if the cyclic shear loading force is smaller.

In some embodiments, the lipid-coated silk microsphere can maintain its lubrication properties (e.g., indicated by coefficient of friction) after subjected to a loading pressure (e.g., a cyclic pressure) of at least about 60 MPa or higher, for at least about 100 cycles or more, including, e.g., at least about 200 cycles, at least about 300 cycles, at least about 400 cycles, at least about 500 cycles or more. It will be readily understood to one of skill in the art that the lipid-coated silk microsphere can maintain its lubrication properties (e.g., indicated by coefficient of friction) much longer, if the loading pressure is smaller.

Any art-recognized naturally-occurring or synthetic lipid component can generally be used to form a lipid coating of the lipid-coated silk microsphere. For example, any lipid component that can form a liposome in an aqueous solution can be used to form a lipid coating of the lipid-coated silk microsphere. In some embodiments, the lipid component can comprise one or more phospholipids. Non-limiting examples of phospholipids include, but are not limited to, phosphatidylcholine; phosphatidylethanolamine; phosphatidylserine; phosphatidylinositol; phosphatidic acid; palmitoyloleoyl phosphatidylcholine; lysophosphatidylcholine; lysophosphatidylethanolamine; dipalmitoylphosphatidylcholine; dioleoylphosphatidylcholine; distearoylphosphatidylcholine; dilinoleoylphosphatidylcholine; 1,2-dioleoyl-sn-glycero-3-phosphocholine (DOPC); 1,2-dioleoyl-sn-glycero-3-phosphoethanolamine (DOPE); 1,2-dilauroyl-sn-glycero-3-phosphocholine (DLPC); 1,2-dimyristoyl-sn-glycero-3-phosphocholine (DMPC); 1,2-dipalmitoylphosphtidylcholine (DPPC), and any combinations thereof. In one embodiment, said at least one lipid component comprises 1,2-dioleoyl-sn-glycero-3-phosphocholine (DOPC). Additional examples of lipid components that can be used to form a lipid-based coating are described in the section "Examples of lipid components" below.

Figure 5:
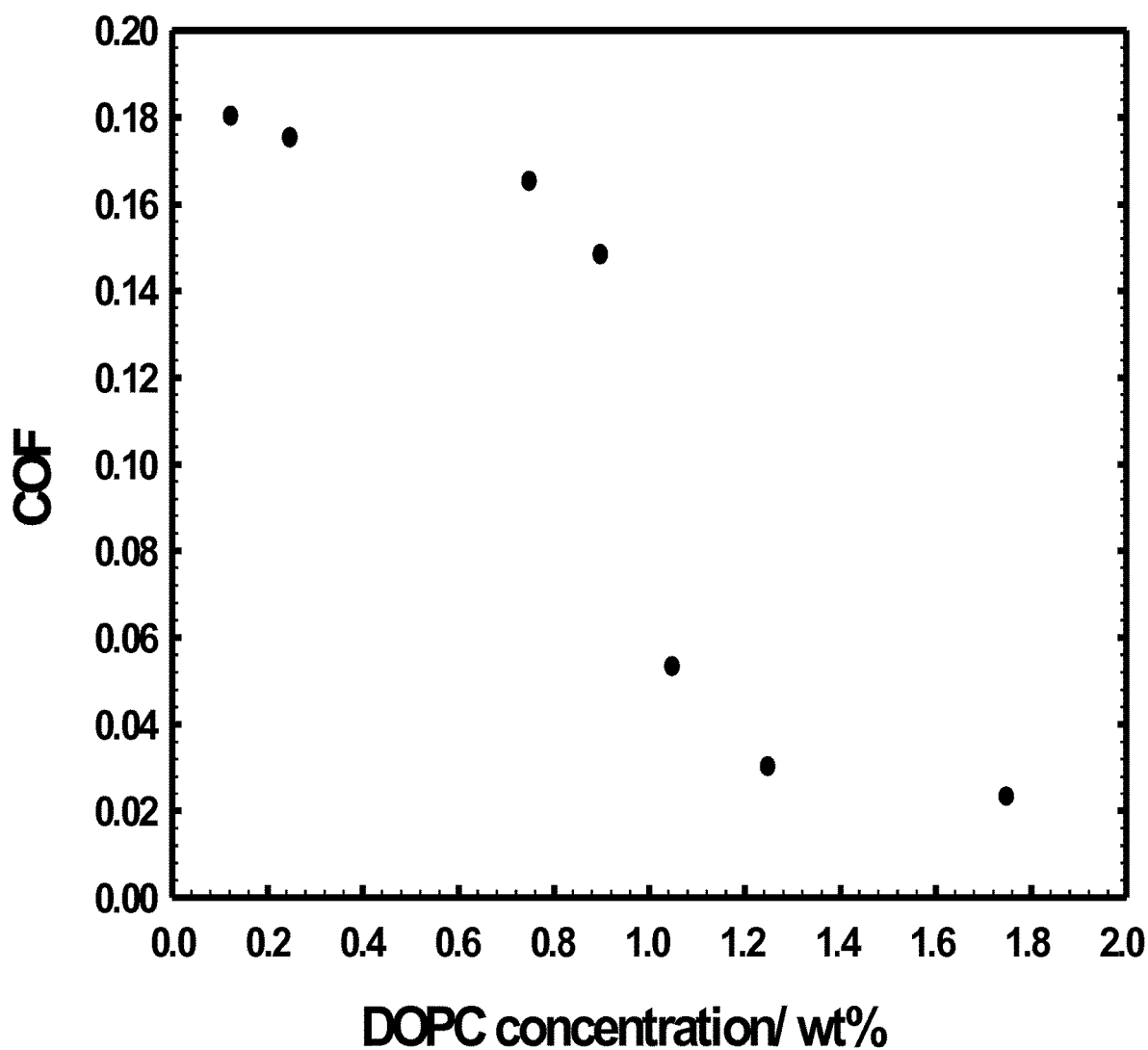
FIG. 5 is a plot showing friction coefficient obtained in friction tests in which DOPC-coated PVA-silk microspheres were used as lubricants. Various DOPC concentrations were assessed to obtain the optimal coating condition.
Figure 16:
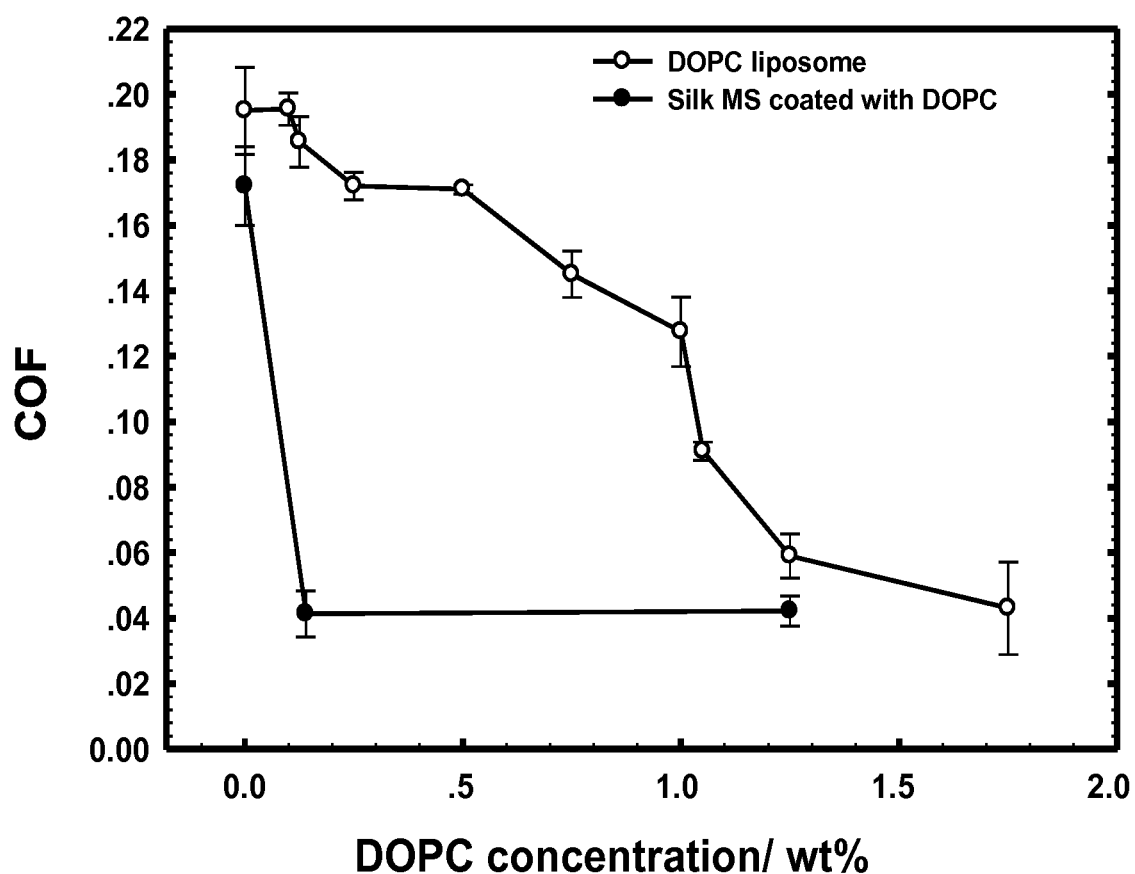
FIG. 16 is a plot showing COF of DOPC liposome and DOPC-coated silk microspheres prepared with different DOPC concentrations.
Figure 17:
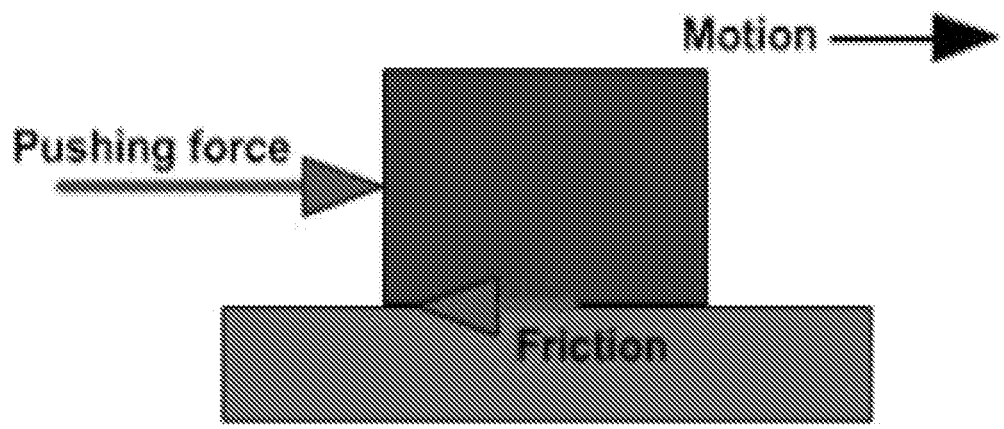
FIG. 17 is a schematic showing that, without wishing to be bound by theory, lipid-coated silk microspheres can lubricate the surface by rolling mechanism, which generally produce much lower friction than sliding.
Figure 17:
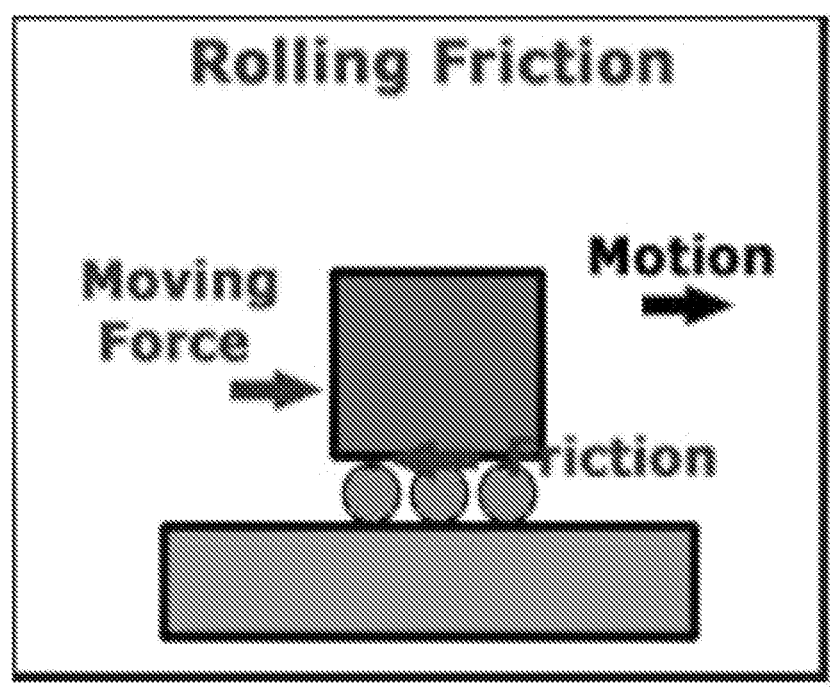
Figures 18A, 18B, 18C, 18D, 18E, 18F, 18G, 18H, 18I, 18J:
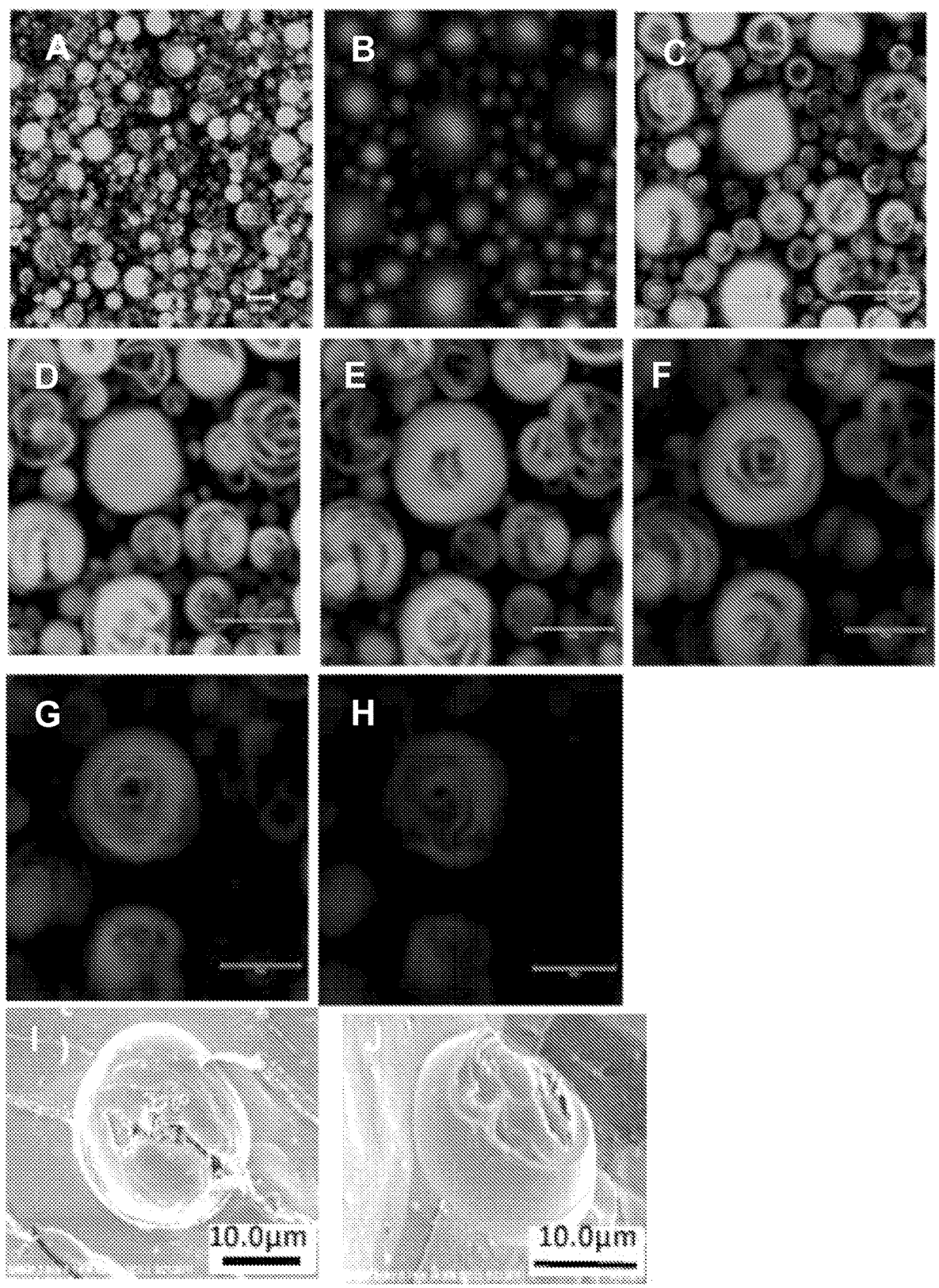
FIGS. 18A-18J is a set of images taken by confocal laser scanning microscopy on the silk microspheres with DOPC (and 1,2-dioleoyl-sn-glycero-3-phosphoethanolamine-N-(carboxyfluorescein)) coating (washed with DI water 3 times).
Figure 19:
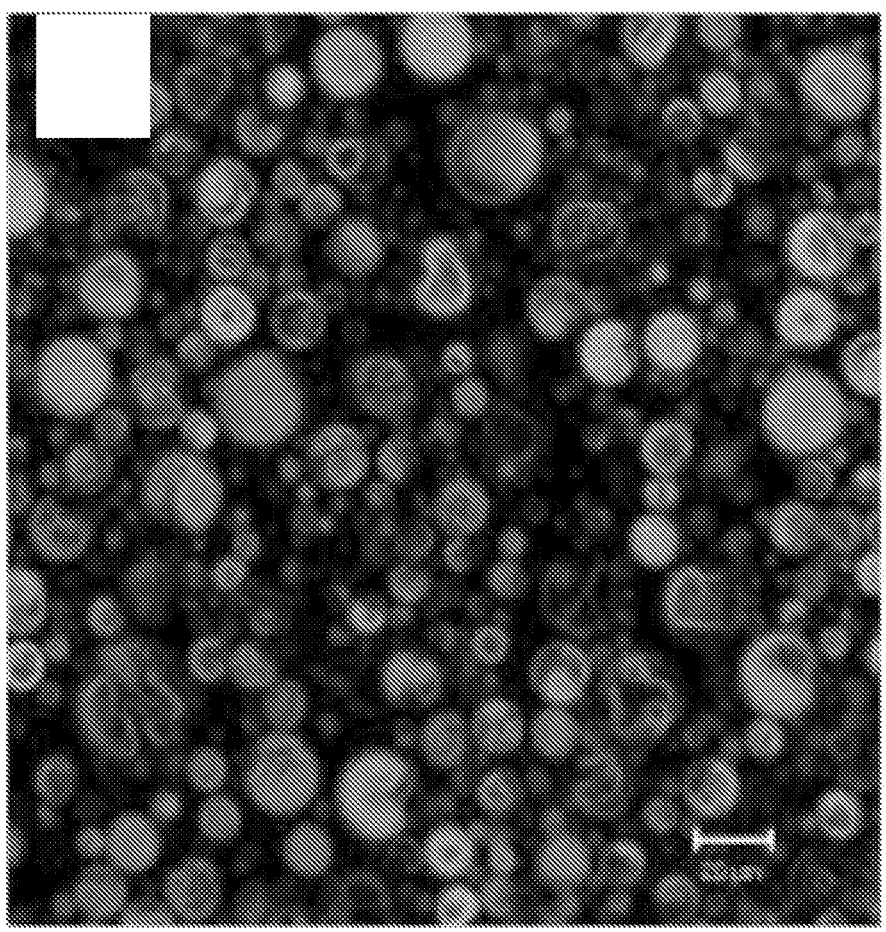
FIG. 19 is an image taken by confocal laser scanning microscopy on the silk microspheres with DOPC (and 1,2-dioleoyl-sn-glycero-3-phosphoethanolamine-N-(carboxyfluorescein)) coating.

The lipid-coated silk microsphere can have lipid component(s) in any amount that is sufficient to yield a desirable coefficient of friction. In general, the coefficient of friction of a lipid-coated silk microsphere against a surface decreases as the concentration of the lipid component in the lipid-coated silk microsphere increases. In some embodiments, the amount of the lipid component present in the silk microsphere (e.g., on its surface) can range from about 0.01 wt % to about 10 wt %, or about 0.05 wt % to about 5 wt %. In some embodiments, the amount of the lipid component present in the silk microsphere (e.g., on its surface) can range from about 0.05 wt % to about 2 wt %. The amount of the lipid component present on the surface of the silk microsphere can be optimized by varying the concentration of the lipid component on the surface of the silk microsphere and measuring the corresponding coefficient of friction, e.g., as shown in FIGS. 5 and 16.

In some embodiments, the lipid-coated silk microsphere and/or the composition can further comprise an additive or active agent. The additive or active agent can be present on the lipid-based coating, the silk fibroin-based microsphere, or a combination thereof, and/or can be independently present in the composition described herein. Exemplary additives or active agents that can be included in the lipid-coated silk microsphere and/or the composition include, without limitations, biopolymers, nanoparticles (e.g., gold nanoparticles), proteins, peptides, nucleic acids (e.g., DNA, RNA, siRNA, modRNA), nucleic acid analogs, nucleotides, oligonucleotides, peptide nucleic acids (PNA), aptamers, antibodies or fragments or portions thereof (e.g., paratopes or complementarity-determining regions), antigens or epitopes, hormones, hormone antagonists, growth factors or recombinant growth factors and fragments and variants thereof, cytokines, enzymes, small molecules, antibiotics or antimicrobial compounds, toxins, therapeutic agents and prodrugs (e.g., but not limited to therapeutic agents for treatment of a joint disorder), small molecules, cells, naturally-occurring or synthetic lubricants (e.g., but not limited to, hyaluronic acid, lubricin), lipid components described herein, polyvinyl alcohol (PVA), an plasticizer (e.g., but not limited to glycerol) and any combinations thereof.

In some embodiments, the additive or active agent can be dispersed homogeneously or heterogeneously within silk fibroin, or dispersed in a gradient, e.g., using the carbodiimide-mediated modification method described in the U.S. Patent Application No. US 2007/0212730. In some embodiments, the active agent can be coated on a surface of the lipid-coated silk microsphere, e.g., via diazonium coupling reaction (see, e.g., U.S. Patent Application No. US 2009/0232963), and/or avidin-biotin interaction (see, e.g., International Application No.: WO 2011/011347). In some embodiments, the additive and/or active agent described herein and below can be stabilized in a lipid-coated silk microsphere described herein. See, e.g., the International Patent Application No. WO/2012/145739 for compositions and methods for stabilization of active agents with silk fibroin. In some embodiments, an active agent can be genetically fused to silk fibroin to form a fusion protein. The contents of the aforementioned patent applications are incorporated herein by reference.

Any amounts of an additive or active agent can be present in a lipid-coated silk microsphere and/or in the composition described herein. For example, in some embodiments, an additive or active agent can be present in the lipid-coated silk microsphere and/or in the composition at a concentration of about 0.001 wt % to about 50 wt %, about 0.005 wt % to about 40 wt %, about 0.01 wt % to about 30 wt %, about 0.05 wt % to about 20 wt %, about 0.1 wt % to about 10 wt %, or about 0.5 wt % to about 5 wt %.

Silk fibroin protein is a natural biopolymer that is produced by silkworms to form the core component of silk fibers [15, 16]. Following a purification procedure, self-assembled silk fibroin protein in the fibers can be disassembled and unfolded into a random coil structure in solution, which can further be fabricated into different material forms, such as porous scaffolds, hydrogels, micro-/nano-spheres, etc [17]. After the fabrication, silk random coil structure is converted to crystalline beta-sheet structure, thus conferring robust mechanical properties to silk materials. Along with other unique properties, such as slow degradation, excellent biocompatibility, multiple reaction sites, etc., silk biomaterials can be used to provide a variety of advantages over other biomaterials for biomedical applications, ranging from tissue regeneration to drug delivery.

In some embodiments, the phospholipid-coated silk microspheres and/or nanospheres can comprise an active agent. In some embodiments, an active agent can include a therapeutic agent for treatment of a joint disorder, e.g., reducing at least one symptom associated with a joint disorder, e.g., inflammation.

As used herein, the term "silk fibroin" includes silkworm fibroin and insect or spider silk protein. See e.g., Lucas et al., 13 Adv. Protein Chem. 107 (1958). Any type of silk fibroin can be used according to different aspects described herein. Silk fibroin produced by silkworms, such as *Bombyx mori*, is the most common and represents an earth-friendly, renewable resource. For instance, silk fibroin used in a silk fibroin-based material can be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that can be used. In some embodiments, silk fibroin can be derived from other sources such as spiders, other silkworms, bees, and bioengineered variants thereof. In some embodiments, silk fibroin can be extracted from a gland of silkworm or transgenic silkworms (see, e.g., WO 2007/098951).

In some embodiments, the silk fibroin can include an amphiphilic peptide. In other embodiments, the silk fibroin can exclude an amphiphilic peptide. "Amphiphilic peptides" possess both hydrophilic and hydrophobic properties. Amphiphilic molecules can generally interact with biological membranes by insertion of the hydrophobic part into the lipid membrane, while exposing the hydrophilic part to the aqueous environment. In some embodiment, the amphiphilic peptide can comprise a RGD motif. An example of an amphiphilic peptide is a 23RGD peptide having an amino acid sequence: HOOC-Gly-ArgGly-Asp-Ile-Pro-Ala-Ser-Ser-Lys-Gly-Gly-Gly-SerArg-Leu-Leu-Leu-Leu-Leu-Leu-Arg-NH2. Other examples of amphiphilic peptides include the ones disclosed in the U.S. Patent App. No.: US 2011/0008406, the content of which is incorporated herein by reference.

Silk fibroin can be present in a lipid-coated silk microsphere described herein at any concentration. In some embodiments, silk fibroin can be present in a lipid-coated silk microsphere described herein in an amount of about 0.1 wt % to about 50 wt %, about 1 wt % to about 45 wt %, about 5 wt % to about 40 wt %, or about 10 wt % to about 35 wt %, of the total weight. In some embodiments, silk fibroin can be present in a lipid-coated silk microsphere described herein in an amount of about 10 wt % to about 99 wt % or higher, about 40 wt % to about 95 wt %, about 50 wt % to about 90 wt %, of the total weight. In some embodiments, silk fibroin can be present in a lipid-coated silk microsphere described herein in an amount of at least about 5%, at least about 8%, at least about 10 wt %, at least about 15 wt %, at least about 20 wt %, at least about 25 wt %, at least about 30 wt %, at least about 35 wt %, at least about 40 wt %, at least about 45 wt %, at least about 50 wt %, at least about 60 wt %, at least about 70 wt %, at least about 80 wt %, at least about 90 wt %, at least about 95 wt % or higher, of the total weight.

In various embodiments, the silk fibroin can be modified for different applications and/or desired mechanical or chemical properties (e.g., to facilitate formation of a gradient of an additive (e.g., an active agent) in silk fibroin-based materials). One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interaction. Exemplary chemical modification methods include, but are not limited to, carbodiimide coupling reaction (see, e.g. U.S. Patent Application. No. US 2007/0212730), diazonium coupling reaction (see, e.g., U.S. Patent Application No. US 2009/0232963), avidin-biotin interaction (see, e.g., International Application No.: WO 2011/011347) and pegylation with a chemically active or activated derivatives of the PEG polymer (see, e.g., International Application No. WO 2010/057142). Silk fibroin can also be modified through gene modification to alter functionalities of the silk protein (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic-inorganic composite. See WO 2006/076711. In some embodiments, the silk fibroin can be genetically modified to be fused with a protein, e.g., a therapeutic protein. Additionally, the silk fibroin-based material can be combined with a chemical, such as glycerol, that, e.g., affects flexibility of the material. See, e.g., WO 2010/042798, Modified Silk films Containing Glycerol. The contents of the aforementioned patent applications are all incorporated herein by reference.

In some embodiments, a lipid-coated silk microsphere can further comprise at least one biopolymer, including at least two biopolymers, at least three biopolymers or more. For example, a lipid-coated silk microsphere can comprise one or more biopolymers in a total concentration of about 0.5 wt % to about 70 wt %, about 5 wt % to about 60 wt %, about 10 wt % to about 50 wt %, about 15 wt % to about 45 wt % or about 20 wt % to about 40 wt %. In some embodiments, the biopolymer(s) can be incorporated homogenously or heterogeneously into the lipid-coated silk microsphere. In other embodiments, the biopolymer(s) can be coated on at least a portion of the surface of the lipid-coated silk microsphere. In any embodiments, the biopolymer(s) can be covalently or non-covalently linked to silk fibroin in a lipid-coated silk microsphere. In some embodiments, the biopolymer(s) can be blended with silk fibroin within a lipid-coated silk microsphere. Examples of the biopolymer can include biocompatible and/or biodegradable polymer, e.g., but are not limited to, polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid, other biocompatible and/or biodegradable polymers and any combinations thereof. See, e.g., International Application Nos.: WO 04/062697; WO 05/012606. The contents of the international patent applications are all incorporated herein by reference. Depending on various applications (e.g., in a wound dressing), in some embodiments, a lipid-coated silk microsphere can include about 1% to about 50%, or about 2% to about 3% to about 10% polyethylene oxide (e.g., PEO with a molecular weight of about 500,000 to about 1,500,000). In other embodiments, the silk fibroin/PEO blend ratio in a lipid-coated silk microsphere can vary from about 1:100 to about 100:1. In some embodiments, the silk fibroin/PEO blend ratio in a lipid-coated silk microsphere can vary from about 2:1 to about 4:1. See, e.g., International Application No.: WO 2011/008842, the content of which is incorporated herein by reference.

In some embodiments, the silk fibroin-based microsphere can comprise a porous structure.

Examples of Lipid Components

Any naturally-occurring or synthetic lipid components can be present in a lipid-coated silk microsphere described herein. The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids. In some embodiments, the lipids also encompass amphiphatic lipid, neutral lipid, non-cationic lipid, anionic lipid and hydrophobic lipid described below. Any one or combination (e.g., 2, 3, 4, 5, or more) of the lipid components described herein can be present in lipid-coated silk microspheres described herein.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and beta-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

Lipids useful in the invention are described, for example, in U.S. Pat. No. 8,283,333, which is incorporated herein.

In some embodiments, a phospholipid can include a glycerophospholipids. In some embodiments, a phospholipid can include a combination of two or more glycerophospholipids. In some embodiments, a glycerophospholipid is selected from the group consisting of phosphatidic acid (phosphatidate) (PA), phosphatidylethanolamine (cephalin) (PE), phosphatidylcholine (lecithin) (PC), phosphatidylserine (PS), and phosphoinositides. In some embodiments, the phospholipid is a phosphosphingolipid. In some embodiments, the phosphosphingolipid is select from the group consisting of ceramide phosphorylcholine (Sphingomyelin) (SPH), ceramide phosphorylethanolamine (Sphingomyelin) (Cer-PE), and ceramide phosphorylglycerol.

Methods of Use and Pharmaceutical Compositions

The phospholipid-coated silk microspheres and/or nanospheres described herein can be used as a lubricant in any place or situation where it is desirable to reduce friction between two or more surfaces. In some embodiments, the phospholipid-coated silk microspheres and/or nanospheres described herein can be used as a lubricant between two or more surfaces of parts present in an equipment, a machine, or any structure. In some embodiments, the phospholipid-coated silk microspheres and/or nanospheres described herein can be used as a biolubricant between two or more surfaces of a biological tissue in a subject in vivo. For example, the phospholipid-coated silk microspheres and/or nanospheres described herein can be placed (e.g., by injection, e.g., intra-articular injection) into a joint (e.g., a damaged or diseased joint) to reduce the friction between two cartilage surfaces, thus relieving the symptoms such as pain and inflammation.

As discussed above, a suspension of the lipid-coated silk microspheres described herein possesses lubrication properties. Accordingly, another aspect described herein relates to methods of reducing friction between two surfaces. The method comprises placing between a first surface and a second surface a composition comprising at least one lipid-coated silk microsphere described herein. In some embodiments, the placement of the composition described herein can reduce friction between the first surface and the second surface by at least about 10% or more, as compared to the friction between the two surfaces without the composition. In some embodiments, the method can further comprise shearing the composition between the first surface and the second surface.

In addition to lubrication properties, the inventors have also discovered anti-wearing effect of the lipid-coated silk microspheres described herein (e.g., DOPC-coated silk microspheres). For example, in a friction test, the wear pattern formed after shearing a glass probe against a silicon surface under cyclic shear loading was less prevalent in the presence of the lipid-coated silk microspheres (e.g., DOPC-coated silk microspheres) than in the presence of the lipid liposomes alone as the lubricant. Thus, during a shear, the lipid-coated silk microsphere within the composition can reduce, e.g., by at least about 10% or more, wearing of either one or both of the first surface and the second surface, as compared to when a lipid-coated non-silk microsphere is used.

In some embodiments, the first surface and the second surface can be present in a mammalian subject. For example, the first surface and the second surface can comprise opposing surfaces of a joint. Thus, a method of treating a joint disorder in a subject is also provided herein. The method comprises placing between two joint surfaces one or more embodiments of the composition described herein, thereby reducing friction between the two joint surfaces. Examples of a joint disorder that can be treated with the compositions described herein include, but not limited to, osteoarthritis (primary (idiopathic) or secondary), rheumatoid arthritis, joint injury (e.g., traumatic or repetitive motion injury), cartilage pathology (e.g. chondrocalconsis, chondromalacia), septic arthritis, arthritis, traumatic cartilage lesions, or any combinations thereof. In one embodiment, the joint disorder that can be treated with one or more embodiments of the compositions described herein is arthritis.

The terms "treatment" and "treating" as used herein, means preventing the progression of the disease, or altering the course of the disorder (for example, but are not limited to, slowing the progression of the disorder), or reversing a symptom of the disorder or reducing one or more symptoms and/or one or more biochemical markers in a subject, preventing one or more symptoms from worsening or progressing, promoting recovery or improving prognosis. For example, in the case of treating a joint disorder, e.g., arthritis, therapeutic treatment refers to reduced pain or discomfort associated with the joint disorder after administration of one or more embodiments of the composition described herein. In another embodiment, the therapeutic treatment refers to alleviation of at least one symptom associated with a joint disorder, e.g., arthritis. Measurable lessening includes any statistically significant decline in a measurable marker or symptom, such as measuring bone loss at the edges of joints—called erosions—combined with loss of joint cartilage with X-ray after treatment. In one embodiment, at least one symptom of a joint disorder, e.g., arthritis, is alleviated by at least about 10%, at least about 15%, at least about 20%, at least about 30%, at least about 40%, or at least about 50%. In another embodiment, at least one symptom is alleviated by more than 50%, e.g., at least about 60%, or at least about 70%. In one embodiment, at least one symptom is alleviated by at least about 80%, at least about 90% or greater, as compared to a control (e.g. in the absence of the composition described herein).

For in vivo administration, the composition comprising a lipid-coated silk microsphere described herein can be injected and/or implanted between two surfaces of a joint to be treated. Thus, the composition comprising a lipid-coated silk microsphere can act as a lubricant to reduce friction between the two joint surfaces and/or to reduce further wear of the bone surfaces and/or cartilages at the joint.

For administration to a subject (e.g., by injection or implantation), the composition comprising a lipid-coated silk microsphere can be formulated in pharmaceutically acceptable compositions which comprise the lipid-coated silk microsphere formulated together with one or more pharmaceutically acceptable carriers (additives) and/or diluents. The pharmaceutical composition can be specially formulated for administration in gel, suspension, cream, solution, liquid or any injectable form. In some embodiments, the pharmaceutical composition can be formulated for intra-articular administration (e.g., by injection or implantation).

As used herein, the term "injectable" generally refers to a composition that can be delivered or administered into a tissue with a minimally invasive procedure. The term "minimally invasive procedure" refers to a procedure that is carried out by entering a subject's body through the skin or through a body cavity or an anatomical opening, but with the smallest damage possible (e.g., a small incision, injection). In some embodiments, the injectable composition can be administered or delivered into a target site between two surfaces by injection, e.g., intra-articular injection. In some embodiments, the injectable composition can be delivered into a target site between two surfaces through a small incision on the skin followed by insertion of a needle, a cannula, and/or tubing, e.g., a catheter. Without wishing to be limited, the injectable composition can be administered or placed into a tissue by surgery, e.g., implantation. In some embodiments, the injectable compositions can comprise at least one active agent described herein. In some embodiments, the injectable compositions can further comprise a pharmaceutically acceptable carrier.

As used herein, the term "pharmaceutically acceptable carrier" refers to a pharmaceutically-acceptable material, composition or vehicle for administration of the lipid-coated silk microspheres, and optionally an active agent. Pharmaceutically acceptable carriers include any and all solvents, dispersion media, coatings, antibacterial and antifungal agents, and isotonic and absorption delaying agents, which are compatible with the lipid-coated silk microspheres and the activity of the active agent, if any, and are physiologically acceptable to the subject. The pharmaceutical formulations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS). In some embodiments, the carrier can include cells.

Additionally, various additives which enhance the stability, sterility, and isotonicity of the injectable compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it may be desirable to include isotonic agents, for example, sugars, sodium chloride, and the like. The injectable compositions can also contain auxiliary substances such as wetting or emulsifying agents, pH buffering agents, gelling or viscosity enhancing additives, preservatives, colors, and the like, depending upon the preparation desired. Standard texts, such as "REMINGTON'S PHARMACEUTICAL SCIENCE", 17th edition, 1985, incorporated herein by reference, may be consulted to prepare suitable preparations, without undue experimentation. Viscosity of the injectable compositions can be maintained at the selected level using a pharmaceutically acceptable thickening agent. In one embodiment, methylcellulose is used because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected, and the desired viscosity for injection. The important point is to use an amount which will achieve the selected viscosity, e.g., addition of such thickening agents into some embodiments of the injectable compositions. Typically, any additives (in addition to the lipid-coated silk microspheres described herein and/or additional active agents) can be present in an amount of 0.001 to 50 wt % dry weight or in a buffered solution. In some embodiments, the active agent can be present in the order of micrograms to milligrams to grams, such as about 0.0001 to about 5 wt %, about 0.0001 to about 1 wt %, about 0.0001 to about 0.05 wt % or about 0.001 to about 20 wt %, about 0.01 to about 10 wt %, and about 0.05 to about 5 wt %. For any pharmaceutical composition comprising an active agent (e.g., a therapeutic agent) to be administered to a subject in need thereof, it is preferred to determine toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan.

Methods of Making Lipid-Coated Silk Microspheres

The lipid-coated silk microspheres in the compositions described herein can be prepared by any methods known in the art, e.g., but not limited to, spray-drying, emulsion-solvent evaporation, and polyvinyl alcohol (PVA) phase separation [18-20]. For example, a lipid coating can be formed on the surface of the silk microspheres during the microsphere preparation and/or post-preparation of the silk microspheres.

In some embodiments, a lipid-coated silk microsphere can be produced by a method using a lipid composition to form a template, the method comprising: (a) sonicating a mixture comprising a silk fibroin solution and a lipid composition, thereby forming a suspension comprising lipid-coated silk microspheres; and (b) lyophilizing at least a portion of the lipid-coated silk microspheres.

The concentration of the lipid composition in the mixture can vary, e.g., with a desired amount of lipid components formed on the coating. In some embodiments, the concentration of the lipid composition in the mixture can vary from about 5 wt % to about 50 wt %, or about 10 wt % to about 30 wt %. In one embodiment, the concentration of the lipid composition in the mixture can be about 20 wt %.

In some embodiments, the silk microspheres can be produced by using a lipid as a template. In some embodiments, the silk microspheres and/or nanospheres can be produced by using a lipid particle as a template.

In some embodiments, the silk microspheres can be produced by using a glycolipid. In some embodiments, the glycolipid is a glyceroglycolipid, a glycosphingolipids, or a glycosylphosphatidylinositols.

In some embodiments, the silk microspheres can be produced by using a sulfolipid.

In some embodiments, the silk microspheres can be produced by using a glycoprotein. In some embodiments, the glycoprotein is N-glycosylated. In some embodiments, the glycoprotein in O-glycosylated.

In some embodiments, the silk microspheres can be produced by using a glycopeptide. In some embodiments, the glycopeptide is a N-linked glycan. In some embodiments, the glycopeptide is an O-linked glycan. In some embodiments, the glycopeptide is a C-linked glycan.

In some embodiments, the silk microspheres can be produced by using a phospholipid as a template. In some embodiments, a phospholipid can include, but are not limited to, DOPC. Using a natural phospholipid, DOPC, as templates, silk microspheres with an average size of about 2-3 μm can be prepared in a simple and all-aqueous manner [21]. When the DOPC thin film was hydrated by silk solution, DOPC multi-lamellar vesicles formed spontaneously with silk microspheres being encapsulated, indicating silk is highly compatible with phospholipids in forming spherical structures. An exemplary method of producing a silk microsphere and/or nanosphere can be found, e.g., in PCT Application No. WO 2008/118133, the content of which is incorporated herein by reference.

However, in accordance with some embodiments described herein, the method described in the PCT Application No. WO 2008/118133 can be modified to narrow the size distribution of microspheres or nanospheres and/or increase the extent of or to maintain a phospholipid coating (template) on silk microspheres such that a phospholipid-coated silk microsphere or nanosphere is produced, e.g., for lubrication (such as joint lubrication). For example, the silk-phospholipid mixture can be subjected to sonication, and optionally followed by centrifugation.

In alternative embodiments, the silk microspheres can be produced by the PVA phase separation method. An exemplary PVA phase separation method for producing a silk microsphere and/or nanosphere can be found, e.g., in PCT Application No. WO 2011/041395, the content of which is incorporated herein by reference. However, in accordance with some embodiments described herein, the method described in the PCT Application No. WO 2011/041395 can be modified to lyophilize the silk and PVA mixture. Without wishing to be bound by theory, lyophilization can generate silk particles with a more porous structure and/or a larger volume. The silk microspheres and/or nanospheres produced by a PVA phase separation method can further be coated with a phospholipid, e.g., but not limited to DOPC, to form a phospholipid-coated silk microsphere and/or nanosphere for lubrication, e.g., for joint lubrication.

Accordingly, in some embodiments, a lipid-coated silk microsphere can be produced by a method based on PVA phase separation, the method comprising: (a) sonicating a mixture comprising a silk fibroin solution and a polyvinyl alcohol (PVA) solution; (b) lyophilizing the mixture; (c) dissolving the lyophilized mixture in an aqueous solution; (d) removing at least a portion of the PVA, thereby forming a silk microsphere; and (e) sonicating the silk microsphere with a hydrated lipid composition, thereby forming a lipid-coated silk microsphere.

The final concentration of the hydrated lipid composition in the mixture can vary, e.g., with a desired amount of lipid components formed on the coating. In some embodiments, the final concentration of the hydrated lipid composition in the mixture can range from about 0.05 wt % to about 10 wt %, or from about 0.1 wt % to about 2 wt %.

In some embodiments, the final concentration of the PVA solution in the mixture can vary from about 0.5 wt % to about 20 wt %, or from about 1 wt % to about 10 wt %.

Depending on the concentrations of the silk fibroin solution and the polyvinyl alcohol (PVA) solution, the volume ratio of the silk fibroin solution to the PVA solution can vary accordingly, provided that the final concentrations of the silk fibroin solution and the PVA solution are satisfied as described above. In some embodiments, the volume ratio of the silk fibroin solution to the PVA solution is about 1:1 to about 1:10, or about 1:2 to about 1:5. In one embodiment, the volume ratio of the silk fibroin solution to the PVA solution is about 1:4.

In some embodiments of the different methods for making a lipid-coated silk microsphere (e.g., the lipid template-based and PVA phase separation-based methods), the method can further comprise separating the smaller-sized lipid-coated silk microspheres from the larger-sized lipid-coated microspheres. For example, for the lipid template-based methods, the method can further comprise separating the smaller-sized lipid-coated silk microspheres form the larger-sized lipid-coated microspheres prior to lyophilization. For the PVA phase separation-based methods, the method can further comprise separating the smaller-sized lipid-coated silk microspheres from the larger-sized lipid-coated microspheres after the silk microsphere is formed, e.g., prior to coating the silk microsphere with a lipid composition. Methods for separating particles based on sizes are known in the art, including, e.g., but not limited to, sieving, filtration, and/or centrifugation, and can be used herein to separate smaller-sized lipid-coated silk microspheres from the larger-sized lipid-coated microspheres. In one embodiment, the smaller-sized lipid-coated silk microspheres can be separated from the larger-sized lipid-coated silk microspheres by centrifugation.

The silk fibroin solution can have any concentration that is suitable to form silk microspheres that can act as lubricants and sustain cyclic shear loading. In some embodiments, the silk fibroin solution can have a concentration of about 1 wt % to about 30 wt %, or a concentration of about 3 wt % to about 15 wt %.

As noted above, one or more naturally-occurring or synthetic lipid components can be used to form a lipid coating on the silk microspheres described herein. For example, one or more naturally-occurring or synthetic lipid components that can form liposomes can be used to form a lipid coating on the silk microspheres described herein. In some embodiments, the lipid composition can comprise one or more phospholipids. Examples of said one or more phospholipids include, but are not limited to, phosphatidylcholine; phosphatidylethanolamine; phosphatidylserine; phosphatidylinositol; phosphatidic acid; palmitoyloleoyl phosphatidylcholine; lysophosphatidylcholine; lysophosphatidylethanolamine; dipalmitoylphosphatidylcholine; dioleoylphosphatidylcholine; distearoylphosphatidylcholine; dilinoleoylphosphatidylcholine; 1,2-dioleoyl-sn-glycero-3-phosphocholine (DOPC); 1,2-dioleoyl-sn-glycero-3-phosphoethanolamine (DOPE); 1,2-dilauroyl-sn-glycero-3-phosphocholine (DLPC); 1,2-dimyristoyl-sn-glycero-3-phosphocholine (DMPC); and any combinations thereof. Additional lipid components described in the section "Examples of lipid components" can also be used to form lipid-coated silk microspheres described herein.

The silk fibroin solution can be prepared by any conventional method known to one skilled in the art. For example, B. mori cocoons are boiled for varying times (e.g., about 10 minutes to about 60 minutes, depending on the form of the silk fibroin-based material to be produced) in an aqueous solution. In one embodiment, the aqueous solution is about 0.02M Na2CO3. The cocoons are rinsed, for example, with water to extract the sericin proteins and the extracted silk is dissolved in an aqueous salt solution. Salts useful for this purpose include lithium bromide, lithium thiocyanate, calcium nitrate or other chemicals capable of solubilizing silk. In some embodiments, the extracted silk is dissolved in about 8M-12 M LiBr solution. The salt is consequently removed using, for example, dialysis.

If necessary, the solution can then be concentrated using, for example, dialysis against a hygroscopic polymer solution, for example, PEG, a polyethylene oxide, amylose or sericin. In some embodiments, the PEG is of a molecular weight of 8,000-10,000 g/mol and has a concentration of 5 wt %-50 wt % (e.g., about 15 wt %). A slide-a-lyzer dialysis cassette (Pierce, MW CO 3500) can be used. However, any dialysis system can be used. The dialysis can be performed for a time period sufficient to result in a final concentration of aqueous silk solution between about 10 wt %-about 50 wt %. In some embodiments, the dialysis can be performed for a time period sufficient to result in a final concentration of aqueous silk solution at about 30 wt %. In most cases dialysis for 5-20 hours (e.g., ~14 hours) is sufficient and longer dialysis is also permitted. See, for example, International Application No. WO 2005/012606, the content of which is incorporated herein by reference.

Alternatively, the silk fibroin solution can be produced using organic solvents. Such methods have been described, for example, in Li, M., et al., J. Appl. Poly Sci. 2001, 79, 2192-2199; Min, S., et al. Sen'I Gakkaishi 1997, 54, 85-92; Nazarov, R. et al., Biomacromolecules 2004 May-June; 5(3):718-26. For example, an exemplary organic solvent that can be used to produce a silk solution includes, but is not limited to, hexafluoroisopropanol.

In some embodiments, the silk fibroin solution can further comprise an agent, e.g., but not limited to, a biopolymer as described herein, a porogen (e.g., a water-soluble particle such as salt) for creating pores in a silk fibroin-based material, an active agent as described herein or any combinations thereof.

As silk fibroin can generally stabilize active agents, some embodiments of the silk fibroin-based material can be used to encapsulate and/or deliver an active agent. In these embodiments, at least one active agent can be dispersed into a silk fibroin solution. Non-limiting examples of the active agents can include cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, therapeutic agents and prodrugs thereof, small molecules, and any combinations thereof.

In some embodiments, at least one active agent described herein can be added to the silk fibroin solution before further processing into silk fibroin-based materials described herein. In some embodiments, the active agent can be dispersed homogeneously or heterogeneously within the silk fibroin, dispersed in a gradient, e.g., using the carbodiimide-mediated modification method described in the U.S. Patent Application No. US 2007/0212730.

In some embodiments, the lipid-coated silk microsphere can be first formed and then contacted with (e.g., dipped into or incubated with) at least one active agent. In some embodiments, at least one active agent described herein can be coated on an exposed surface of the lipid-coated silk microsphere upon the contacting. In some embodiments, at least one active agent described here can diffuse into the lipid-coated silk microsphere upon the contacting.

In some embodiments, it can be desirable to have the lipid-coated silk microsphere to be porous, i.e., a silk fibroin-based material having a porosity of at least about 30%, at least about 40%, at least about 50%, at least about 60%, at least about 70%, at least about 80%, at least about 90%, or higher. Too high porosity can generally yield a lipid-coated silk microsphere and thus the resulting network thereof with lower mechanical properties, but can allow a release of an active agent embedded therein, if any. One of skill in the art can adjust the porosity accordingly, based on a number of factors such as, but not limited to, desired release rates, molecular size and/or diffusion coefficient of the active agent, and/or concentrations and/or amounts of silk fibroin in a silk-based material. The term "porosity" as used herein is a measure of void spaces in a material, e.g., a silk fibroin-based material, and is a fraction of volume of voids over the total volume, as a percentage between 0 and 100% (or between 0 and 1). Determination of matrix porosity is well known to a skilled artisan, e.g., using standardized techniques, such as mercury porosimetry and gas adsorption, e.g., nitrogen adsorption.

The porous lipid-coated silk microsphere can have any pore size. However, in some embodiments, it can be desirable to have the pore size of the lipid-coated silk microsphere be small enough such that the lipid-coated silk microsphere s embedded therein cannot leak or diffuse out from the silk fibroin-based material, but large enough for an active agent, if any, embedded therein to be released from the silk fibroin-based material, if desirable. In some embodiments, the pores of a lipid-coated silk microsphere can have a size distribution ranging from about 1 nm to about 100 μm, from about 10 nm to about 50 μm, from about 50 nm to about 25 μm, from about 100 nm to about 20 μm, from about 500 nm to about 10 μm, or from about 1 μm to about 5 μm. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. Methods for forming pores in a silk-based material are known in the art, e.g., porogen-leaching method, freeze-drying method, and/or gas-forming method. Such methods are described, e.g., in U.S. Pat. App. Nos.: US 2010/0279112, US 2010/0279112, and U.S. Pat. No. 7,842,780, the contents of which are incorporated herein by reference.

To alter a property of the silk fibroin-based material, post-treatment of the silk fibroin-based material can be employed. For example, post-treatment methods can be applied to the silk fibroin-based material to induce beta-sheet structure formation in silk fibroin and thus modulate physical properties of silk fibroin (e.g., mechanical strength, degradability and/or solubility). Further, such post-treatment to induce formation of beta-sheet conformation structure in silk fibroin can prevent a silk fibroin-based material from contracting into a compact structure and/or forming an entanglement. Examples of various post-treatments can include, without limitations, controlled slow drying (Lu et al., 10 Biomacromolecules 1032 (2009)); water annealing (Jin et al., Water-Stable Silk Films with Reduced Beta-Sheet Content, 15 Adv. Funct. Mats. 1241 (2005); Hu et al. Regulation of Silk Material Structure by Temperature-Controlled Water Vapor Annealing, 12 Biomacromolecules 1686 (2011)); stretching (Demura & Asakura, Immobilization of glucose oxidase with *Bombyx mori* silk fibroin by only stretching treatment and its application to glucose sensor, 33 Biotech & Bioengin. 598 (1989)); compressing; solvent immersion, including methanol (Hofmann et al., Silk fibroin as an organic polymer for controlled drug delivery, 111 J Control Release. 219 (2006)), ethanol (Miyairi et al., Properties of b-glucosidase immobilized in sericin membrane. 56 J. Fermen. Tech. 303 (1978)), glutaraldehyde (Acharya et al., Performance evaluation of a silk protein-based matrix for the enzymatic conversion of tyrosine to L-DOPA. 3 Biotechnol J. 226 (2008)), and 1-ethyl-3-(3-dimethyl aminopropyl) carbodiimide (EDC) (Bayraktar et al., Silk fibroin as a novel coating material for controlled release of theophylline. 60 Eur J Pharm Biopharm. 373 (2005)); pH adjustment, e.g., pH titration and/or exposing a silk-based material to an electric field (see, e.g., U.S. Patent App. No. US2011/0171239); heat treatment; shear stress (see, e.g., International App. No.: WO 2011/005381), ultrasound, e.g., sonication (see, e.g., U.S. Patent Application Publication No. U.S. 2010/0178304, and International Patent Application No. WO2008/150861); constraint-drying (see, e.g., International Patent Application No. WO 2011/008842); and any combinations thereof. Content of all of the references listed above is incorporated herein by reference in their entirety.

In some embodiments, the lipid-coated silk microspheres described herein can be sterilized. Sterilization methods for biomaterials are well known in the art, including, but not limited to, gamma or ultraviolet radiation, autoclaving (e.g., heat/steam); alcohol sterilization (e.g., ethanol and methanol); and gas sterilization (e.g., ethylene oxide sterilization).

Further, the silk fibroin-based material described herein can take advantage of the many techniques developed to functionalize silk fibroin (e.g., active agents such as dyes and sensors). See, e.g., U.S. Pat. No. 6,287,340, Bioengineered anterior cruciate ligament; WO 2004/000915, Silk Biomaterials & Methods of Use Thereof; WO 2004/001103, Silk Biomaterials & Methods of Use Thereof; WO 2004/062697, Silk Fibroin Materials & Use Thereof; WO 2005/000483, Method for Forming inorganic Coatings; WO 2005/012606, Concentrated Aqueous Silk Fibroin Solution & Use Thereof; WO 2011/005381, Vortex-Induced Silk fibroin Gelation for Encapsulation & Delivery; WO 2005/123114, Silk-Based Drug Delivery System; WO 2006/076711, Fibrous Protein Fusions & Uses Thereof in the Formation of Advanced Organic/Inorganic Composite Materials; U.S. Application Pub. No. 2007/0212730, Covalently immobilized protein gradients in three-dimensional porous scaffolds; WO 2006/042287, Method for Producing Biomaterial Scaffolds; WO 2007/016524, Method for Stepwise Deposition of Silk Fibroin Coatings; WO 2008/085904, Biodegradable Electronic Devices; WO 2008/118133, Silk Microspheres for Encapsulation & Controlled Release; WO 2008/108838, Microfluidic Devices & Methods for Fabricating Same; WO 2008/127404, Nanopatterned Biopolymer Device & Method of Manufacturing Same; WO 2008/118211, Biopolymer Photonic Crystals & Method of Manufacturing Same; WO 2008/127402, Biopolymer Sensor & Method of Manufacturing Same; WO 2008/127403, Biopolymer Optofluidic Device & Method of Manufacturing the Same; WO 2008/127401, Biopolymer Optical Wave Guide & Method of Manufacturing Same; WO 2008/140562, Biopolymer Sensor & Method of Manufacturing Same; WO 2008/127405, Microfluidic Device with Cylindrical Microchannel & Method for Fabricating Same; WO 2008/106485, Tissue-Engineered Silk Organs; WO 2008/140562, Electroactive Biopolymer Optical & Electro-Optical Devices & Method of Manufacturing Same; WO 2008/150861, Method for Silk Fibroin Gelation Using Sonication; WO 2007/103442, Biocompatible Scaffolds & Adipose-Derived Stem Cells; WO 2009/155397, Edible Holographic Silk Products; WO 2009/100280, 3-Dimensional Silk Hydroxyapatite Compositions; WO 2009/061823, Fabrication of Silk Fibroin Photonic Structures by Nanocontact Imprinting; WO 2009/126689, System & Method for Making Biomaterial Structures.

In an alternative embodiment, the lipid-coated silk microsphere can include plasmonic nanoparticles to form photothermal elements, e.g., by adding plasmonic particles into a silk solution and forming a lipid-coated silk microsphere therefrom. This approach takes advantage of the superior doping characteristics of silk fibroin. Thermal therapy has been shown to aid in the delivery of various agents, see Park et al., Effect of Heat on Skin Permeability, 359 Intl. J. Pharm. 94 (2008). In one embodiment, short bursts of heat on very limited areas can be used to maximize permeability with minimal harmful effects on surrounding tissues. Thus, plasmonic particle-doped silk fibroin matrices can add specificity to thermal therapy by focusing light to locally generate heat only via the silk fibroin matrices. In some embodiments, the silk fibroin matrices can include photothermal agents such as gold nanoparticles.

A lipid-coated silk microsphere produced by one or more embodiments of the lipid template-based method as well as the PVA phase separation-based method are also provided herein. These lipid-coated silk microspheres can be used as a lubricant to reduce friction between any two surfaces and/or reduce wear over time. In some embodiments, the lipid-coated silk microspheres can be used as a lubricant to reduce friction between any two joint surfaces (e.g., surfaces comprising bone and/or cartilage).

Examples of Additives (e.g., Exemplary Active Agents)

An active agent that can be included in a lipid-coated silk microsphere can represent any material capable of being incorporated in a silk fibroin-based material or in the composition described herein. For example, the active agent can be a therapeutic agent, or a biological material, such as cells (including stem cells such as induced pluripotent stem cells), proteins, peptides, nucleic acids (e.g., DNA, RNA, siRNA), nucleic acid analogs, nucleotides, oligonucleotides, peptide nucleic acids (PNA), aptamers, antibodies or fragments or portions thereof (e.g., paratopes or complementarity-determining regions), antigens or epitopes, hormones, hormone antagonists, growth factors or recombinant growth factors and fragments and variants thereof, cell attachment mediators (such as RGD), cytokines, enzymes, small molecules, antibiotics or antimicrobial compounds, viruses, antivirals, toxins, therapeutic agents and prodrugs, small molecules and any combinations thereof. See, e.g., WO 2009/140588; U.S. Patent Application Ser. No. 61/224,618). The active agent can also be a combination of any of the above-mentioned agents. Encapsulating either a therapeutic agent or biological material, or the combination of them, is desirous because the encapsulated composition can be used for numerous biomedical purposes.

In some embodiments, the active agent can also be an organism such as a fungus, plant, animal, bacterium, or a virus (including bacteriophage). Moreover, the active agent may include neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

Exemplary cells suitable for use herein may include, but are not limited to, progenitor cells or stem cells, smooth muscle cells, skeletal muscle cells, cardiac muscle cells, epithelial cells, endothelial cells, urothelial cells, fibroblasts, myoblasts, ocular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, and precursor cells. The active agents can also be the combinations of any of the cells listed above. See also WO 2008/106485; WO 2010/040129; WO 2007/103442.

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

The term "nucleic acids" used herein refers to polynucleotides such as deoxyribonucleic acid (DNA), and, where appropriate, ribonucleic acid (RNA), polymers thereof in either single- or double-stranded form. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985), and Rossolini, et al., Mol. Cell. Probes 8:91-98 (1994)). The term "nucleic acid" should also be understood to include, as equivalents, derivatives, variants and analogs of either RNA or DNA made from nucleotide analogs, and, single (sense or antisense) and double-stranded polynucleotides. The term "nucleic acid" also encompasses modified RNA (modRNA). The term "nucleic acid" also encompasses siRNA, shRNA or any combinations thereof.

The term "modified RNA" means that at least a portion of the RNA has been modified, e.g., in its ribose unit, in its nitrogenous base, in its internucleoside linkage group, or any combinations thereof. Accordingly, in some embodiments, a "modified RNA" may contain a sugar moiety which differs from ribose, such as a ribose monomer where the 2'-OH group has been modified. Alternatively, or in addition to being modified at its ribose unit, a "modified RNA" may contain a nitrogenous base which differs from A, C, G and U (a "non-RNA nucleobase"), such as T or MeC. In some embodiments, a "modified RNA" may contain an internucleoside linkage group which is different from phosphate (—O—P(O)2-O—), such as —O—P(O,S)—O—.

The term "short interfering RNA" (siRNA), also referred to herein as "small interfering RNA" is defined as an agent which functions to inhibit expression of a target gene, e.g., by RNAi. An siRNA can be chemically synthesized, it can be produced by in vitro transcription, or it can be produced within a host cell. siRNA molecules can also be generated by cleavage of double stranded RNA, where one strand is identical to the message to be inactivated. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense 60 strand and/or the antisense strand. The term "siRNA" includes duplexes of two separate strands, as well as single strands that can form hairpin structures comprising a duplex region.

The term "shRNA" as used herein refers to short hairpin RNA which functions as RNAi and/or siRNA species but differs in that shRNA species are double stranded hairpin-like structure for increased stability. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA.

The term "enzymes" as used here refers to a protein molecule that catalyzes chemical reactions of other substances without it being destroyed or substantially altered upon completion of the reactions. The term can include naturally occurring enzymes and bioengineered enzymes or mixtures thereof. Examples of enzyme families include, but are not limited to, peroxidase, lipase, amylose, organophosphate dehydrogenase, ligases, restriction endonucleases, ribonucleases, DNA polymerases, glucose oxidase, laccase, kinases, dehydrogenases, oxidoreductases, GTPases, carboxyl transferases, acyl transferases, decarboxylases, transaminases, racemases, methyl transferases, formyl transferases, and -ketodecarboxylases.

As used herein, the term "aptamers" means a single-stranded, partially single-stranded, partially double-stranded or double-stranded nucleotide sequence capable of specifically recognizing a selected non-oligonucleotide molecule or group of molecules. In some embodiments, the aptamer recognizes the non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and non-nucleotide residues, groups or bridges. Methods for selecting aptamers for binding to a molecule are widely known in the art and easily accessible to one of ordinary skill in the art.

As used herein, the term "antibody" or "antibodies" refers to an intact immunoglobulin or to a monoclonal or polyclonal antigen-binding fragment with the Fc (crystallizable fragment) region or FcRn binding fragment of the Fc region. The term "antibodies" also includes "antibody-like molecules", such as fragments of the antibodies, e.g., antigen-binding fragments. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

Exemplary antibodies that may be incorporated in silk fibroin include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab. The active agents can also be the combinations of any of the antibodies listed above.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

The expression "linear antibodies" refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The expression "single-chain Fv" or "scFv" antibody fragments, as used herein, is intended to mean antibody fragments that comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. (The Pharmacology of Monoclonal Antibodies, vol. 113, Rosenburg and Moore eds., Springer-Verlag, New York, pp. 269-315 (1994)).

The term "diabodies," as used herein, refers to small antibody fragments with two antigen-binding sites, which fragments comprise a heavy-chain variable domain (VH) Connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. (EP 404,097; WO 93/11161; Hollinger et ah, Proc. Natl. Acad. Sd. USA, P0:6444-6448 (1993)).

As used herein, the term "small molecules" refers to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "antibiotics" or "antimicrobial compound" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics can include, but are not limited to, actinomycin; aminoglycosides (e.g., neomycin, gentamicin, tobramycin); ? lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Optionally, the antibiotic agents may also be antimicrobial peptides such as defensins, magainin and nisin; or lytic bacteriophage. The antibiotic agents can also be the combinations of any of the agents listed above. See also PCT/US2010/026190.

As used herein, the term "antigens" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes. The term "antigen" can also refer to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

As used herein, the term "therapeutic agent" generally means a molecule, group of molecules, complex or substance administered to an organism for diagnostic, therapeutic, preventative medical, or veterinary purposes. As used herein, the term "therapeutic agent" includes a "drug" or a "vaccine." This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term can also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA), ribonucleic acid (RNA), modified DNA or RNA, or mixtures or combinations thereof, including, for example, DNA nanoplexes.

The term "therapeutic agent" also includes an agent that is capable of providing a local or systemic biological, physiological, or therapeutic effect in the biological system to which it is applied. For example, the therapeutic agent can act to control infection or inflammation, enhance cell growth and tissue regeneration, control tumor growth, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism. Additionally, a silk-based composition can contain combinations of two or more therapeutic agents.

In some embodiments, different types of therapeutic agents that can be encapsulated or dispersed in a silk fibroin-based material can include, but not limited to, proteins, peptides, antigens, immunogens, vaccines, antibodies or portions thereof, antibody-like molecules, enzymes, nucleic acids, modified RNA, siRNA, shRNA, aptamers, small molecules, antibiotics, and any combinations thereof.

Exemplary therapeutic agents include, but are not limited to, those found in Harrison's Principles of Internal Medicine, 13th Edition, Eds. T. R. Harrison et al. McGraw-Hill N.Y., N.Y.; Physicians Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990, the complete contents of all of which are incorporated herein by reference.

In some embodiments, the lipid-coated silk microspheres and/or the compositions described herein can further comprise one or more therapeutic agents for treatment of a joint disorder. Examples of therapeutic agents for treatment of a joint disorder described herein include, but are not limited to, non-steroidal anti-inflammatory drugs (NSAIDS), e.g., diclofenac, ibuprofen, piroxicam; anesthetics, e.g., Lidocaine and Bupivacaine; opiod analgesics, e.g., codeine and morphine; corticosteroids, e.g., dexamethasone and prednisone; antineoplastic agents such as methotrexate; antiviral agents, e.g., acyclovir and vidarabine; monoclonal antibodies e.g., Humira® and chimeric monoclonal antibodies, e.g., infliximab, cells (e.g., cartilage-associated cells such as chondroblasts; protein; nucleic acid; minerals, e.g., selenium, strontium; vitamins, e.g., tocopherol; nutraceuticals, e.g., curcumin; other desirable biologically active material; or any combinations thereof.

Embodiments of Various Aspects Described Herein can be Defined in any of the Following Numbered Paragraphs 1. A composition comprising: a silk microsphere coated with a lipid component.
2. The composition of paragraph 1, wherein the lipid-coated silk microsphere yields a static friction coefficient of less than 0.2, as determined by a friction test against a silica surface.
3. The composition of paragraph 1 or 2, wherein the lipid-coated silk microsphere has a width dimension of about 1 µm to about 100 µm.
4. The composition of any of paragraphs 1-3, wherein the lipid-coated silk microsphere has a width dimension of at least about 3 µm or higher.
5. The composition of any of paragraphs 1-4, wherein the lipid-coated silk microsphere is resistant to degradation under cyclic shear loading.
6. The composition of any of paragraphs 1-5, wherein an amount of the lipid present in the silk microsphere ranges from about 0.01 wt % to about 10 wt %.
7. The composition of any of paragraphs 1-6, wherein the lipid coating comprises one or more phospholipids.
8. The composition of paragraph 7, wherein said one or more phospholipids are selected from the group consisting of phosphatidylcholine; phosphatidylethanolamine; phosphatidylserine; phosphatidylinositol; phosphatidic acid; palmitoyloleoyl phosphatidylcholine; lysophosphatidylcholine; lysophosphatidylethanolamine; dipalmitoylphosphatidylcholine; dioleoylphosphatidylcholine; distearoylphosphatidylcholine; dilinoleoylphosphatidylcholine; 1,2-dioleoyl-sn-glycero-3-phosphocholine (DOPC); 1,2-dioleoyl-sn-glycero-3-phosphoethanolamine (DOPE); 1,2-dilauroyl-sn-glycero-3-phosphocholine (DLPC); 1,2-dimyristoyl-sn-glycero-3-phosphocholine (DMPC); and any combinations thereof.
9. The composition of any of paragraphs 1-8, wherein the lipid-coated silk microsphere and/or the composition further comprises an additive or active agent.
10. The composition of paragraph 9, wherein the additive or active agent is present on the lipid coating, the silk microsphere, or a combination thereof.
11. The composition of paragraph 9 or 10, wherein the additive or active agent is selected from the group consisting of biopolymers, nanoparticles (e.g., gold nanoparticles), proteins, peptides, nucleic acids (e.g., DNA, RNA, siRNA, modRNA), nucleic acid analogs, nucleotides, oligonucleotides, peptide nucleic acids (PNA), aptamers, antibodies or fragments or portions thereof (e.g., paratopes or complementarity-determining regions), antigens or epitopes, hormones, hormone antagonists, growth factors or recombinant growth factors and fragments and variants thereof, cytokines, enzymes, small molecules, antibiotics or antimicrobial compounds, toxins, therapeutic agents and prodrugs, small molecules, cells, and any combinations thereof.
12. The composition of any of paragraphs 1-11, wherein the silk microsphere comprises a porous structure.
13. The composition of any of paragraphs 1-12, wherein the lipid-coated silk microsphere is substantially spherical.
14. The composition of any of paragraphs 1-13, wherein the composition is formulated for use in a mammalian subject.
15. The composition of paragraph 14, wherein the composition is formulated for use as a joint lubricant.
16. A method comprising placing between a first surface and a second surface a composition of any of paragraphs 1-15, thereby reducing friction between the first surface and the second surface.
17. The method of paragraph 16, further comprising shearing the composition between the first surface and the second surface.
18. The method of paragraph 16 or 17, wherein the lipid-coated silk microsphere within the composition reduces wearing of either one or both of the first surface and the second surface during a shear, as compared to when a lipid-coated non-silk microsphere is used.
19. The method of any of paragraphs 16-18, wherein the first surface and the second surface are present in a mammalian subject.
20. The method of paragraph 19, wherein the first surface and the second surface are opposing surfaces of a joint.
21. A method of treating arthritis in a subject comprising placing between two joint surfaces a composition of any of paragraphs 1-15, thereby reducing friction between the two joint surfaces.
22. A method of making a lipid-coated silk microsphere comprising:
    a. sonicating a mixture comprising a silk fibroin solution and a lipid composition, thereby forming a suspension comprising lipid-coated silk microspheres; and
    b. lyophilizing at least a portion of the lipid-coated silk microspheres.
23. The method of paragraph, wherein the concentration of the lipid composition in the mixture is about 5 wt % to about 50 wt %, or about 10 wt % to about 30 wt %.
24. A method of making a lipid-coated silk microsphere comprising:
    a. sonicating a mixture comprising a silk fibroin solution and a PVA solution;
    b. lyophilizing the mixture;
    c. dissolving the lyophilized mixture in an aqueous solution;
    d. removing at least a portion of the PVA, thereby forming a silk microsphere; and
    e. sonicating a mixture comprising the silk microsphere and a lipid composition, thereby forming a lipid-coated silk microsphere.
25. The method of paragraph 24, wherein the concentration of the lipid composition in the mixture ranges from about 0.05% wt % to about 10 wt %.
26. The method of paragraph 24 or 25, where the volume ratio of the silk fibroin solution to the PVA solution is about 1:1 to about 10:1.
27. The method of any of paragraphs 24-26, wherein the PVA solution has a concentration of about 1 wt % to about 10 wt %.
28. The method of any of paragraphs 22-27, further comprising separating the smaller-sized lipid-coated silk microspheres from the larger-sized lipid-coated microspheres.
29. The method of paragraph 28, wherein the separating is performed by centrifugation.
30. The method of any of paragraphs 22-29, wherein the lipid composition comprises one or more phospholipids.
31. The method of paragraph 30, wherein said one or more phospholipids are selected from the group consisting of phosphatidylcholine; phosphatidylethanolamine; phosphatidylserine; phosphatidylinositol; phosphatidic acid; palmitoyloleoyl phosphatidylcholine; lysophosphatidylcholine; lysophosphatidylethanolamine; dipalmitoylphosphatidylcholine; dioleoylphosphatidylcholine; distearoylphosphatidylcholine; dilinoleoylphosphatidylcholine; 1,2-dioleoyl-sn-glycero-3-phosphocholine (DOPC); 1,2-dioleoyl-sn-glycero-3-phosphoethanolamine (DOPE); 1,2-dilauroyl-sn-glycero-3-phosphocholine (DLPC); 1,2-dimyristoyl-sn-glycero-3-phosphocholine (DMPC); and any combinations thereof.

32. The method of any of paragraphs 22-31, wherein the silk fibroin solution has a concentration of about 1 wt % to about 30 wt %, or a concentration of about 3 wt % to about 15 wt %.

33. The method of any of paragraphs 22-32, further comprising contacting the lipid-coated silk microsphere with at least one additive or active agent.

34. The method of any of paragraphs 22-33, wherein the silk fibroin solution further comprises an additive or active agent.

35. The method of paragraph 33 or 34, wherein the additive or active agent is selected from the group consisting of biopolymers, nanoparticles (e.g., gold nanoparticles), proteins, peptides, nucleic acids (e.g., DNA, RNA, siRNA, modRNA), nucleic acid analogs, nucleotides, oligonucleotides, peptide nucleic acids (PNA), aptamers, antibodies or fragments or portions thereof (e.g., paratopes or complementarity-determining regions), antigens or epitopes, hormones, hormone antagonists, growth factors or recombinant growth factors and fragments and variants thereof, cytokines, enzymes, small molecules, antibiotics or antimicrobial compounds, toxins, therapeutic agents and prodrugs, small molecules, cells, and any combinations thereof 36. A silk microsphere produced by the method of any of paragraphs 22-35.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the term "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "substantially" means a proportion of at least about 90%, at least about 95%, at least about 98%, at least about 99% or more, or any integer between 90% and 100%. In some embodiments, the term "substantially" can include 100%.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1

Exemplary Materials and Methods

Exemplary Materials.

Degummed silk fibers were purchased from Suhao Biomaterials Technology (Suzhou, China). DOPC was purchased from Aavanti Inc. (Alabaster, Ala.). PVA and all other chemicals were purchased from Sigma-Aldrich (St. Louis, Mo.).

Regenerated Silk Solution.

Degummed silk fibers were dissolved in 9.3 M lithium bromide solution (20 wt. %) at 60° C. for about 4 hours and dialyzed against deionized water for ~2 days [22]. The final silk concentration was approximately 8 wt %. The solution was stored at 4° C. until used to make microspheres.

Preparation of Silk Micro-/Nanospheres:

(1) Preparation Using DOPC.

Silk microspheres were prepared using DOPC as a template as reported in Ref. 21 with some modification. Briefly, ~200 mg of DOPC was dissolved in 2 ml chloroform in a glass tube and dried into a thin film under a flow of nitrogen gas, which was hydrated by adding 1 ml of 8 wt % silk fibroin solution into the tube and pipetting. The resulting milky suspension was diluted 4 times with water and then subjected to sonication using a probe sonifier (Branson Ultrasonics Co., Danbury, Conn.) at ~10% amplitude for ~30 seconds. The homogenized suspension was diluted to 50 ml with ultrapure water, followed by centrifugation at 2,000 rpm for 20 min at 20° C. (Ependorf 5804R centrifuge). The pellet obtained was resuspended in ~50 ml ultrapure water. Along with the supernatant collected (sample LS-1S in Table 1 shown below), the suspension was lyophilized (sample LS-1P). The control sample was prepared in the same way, except that the centrifugation step was eliminated. After the lipid-silk suspension was diluted to ~50 ml, the resulting suspension was directly subjected to lyophilization (sample LS). Various samples and their preparation conditions were listed in Table 1 shown below.

(2) Preparation Using PVA.

PVA-based silk microspheres were prepared as reported in Ref 20 with some modification. Briefly, ~5 wt % silk was mixed with ~5 wt % PVA at a volume ratio of ~4/1, and ~6 ml of the mixture was sonicated in a 15-ml plastic tube using Branson probe sonifier at ~20% amplitude for ~30 seconds prior to lyophilization. The lyophilized material was dissolved in water, and the suspension was centrifuged to remove most of the PVA (readily solubilized in water), leaving the silk micro-/nanospheres in the pellet. The centrifugation was performed at a high speed of ~11,000 rpm for ~20 min at ~20° C. using an Ependorf 5804R centrifuge. The silk microspheres and nanospheres can further be separated from each other by centrifugation at 5,000 rpm for about 20 min. The collected supernatant mostly contained silk nanospheres, while the resuspended pellet mostly contained silk microspheres. Various samples and their preparation conditions were described in Table 1 as shown below.

Characterization of Silk Micro/Nanospheres.

Silk microspheres larger than 1 μm were observed using an optical microscope (Carl Zeiss, Jena, Germany) at a phase contrast mode. The particle size was estimated based on the images. The size of silk nanoparticles were determined by using a particle analyzer (Mastersizer S 300, Malvern, Worcestershire, UK), with the standard lens size range of 0.05-900 μm.

Preparation of DOPC-Coated Silk Microspheres.

Dry DOPC powder was dissolved in chloroform (e.g., ~200 mg of DOPC was dissolved in 2 ml chloroform), and then dried into a thin film in a glass container using a rotary evaporator. The dried film was hydrated with ~0.5 wt % silk microsphere suspension at about 50° C. The final concentration of DOPC in the suspension varied in a range of about 0.1 wt % to about 1.8 wt %. The suspension was probe sonicated for 30 minutes to obtain DOPC-coated silk microspheres. The DOPC-coated silk microspheres were further subjected to washing steps. For example, ~0.5 ml of sonicated suspension was diluted to 50 ml, and then centrifuged at 4000 rpm for 10 minutes using an Eppendorf 5417R centrifuge. The pellet was resuspended in 50 ml ultrapure water and the washing step was repeated at least two more times. Finally the pellet was suspended in 0.5 ml ultrapure water and used for friction tests. A control sample was prepared in the same way as above, except that after sonication and centrifugation, the pellet was resuspended in MeOH, followed by centrifugation to remove the methanol in supernatant that contained free DOPC. The resulting naked silk microspheres were subjected to friction tests.

Friction Test.

A universal materials tester (UMT) was used to measure the friction force and lubrication properties between a spherical glass tip and flat silica wafer (FIG. 1). The two surfaces (glass tip and silica wafer) were immersed in a bath containing DOPC-coated silk microsphere suspension, and the glass tip was pulled horizontally at a controlled velocity while the friction force, F, between the two surfaces is continuously measured. The friction coefficient μ=F/N is calculated and plotted as a function of pulling time (seconds). The static friction coefficient is obtained from the maximum value of the plot.

Example 2

Exemplary Fabrication Methods of DOPC-Coated Silk Particles for Joint Lubrication Control of Silk Particle Sizes.

Figures 2A, 2B, 2C, 2D:
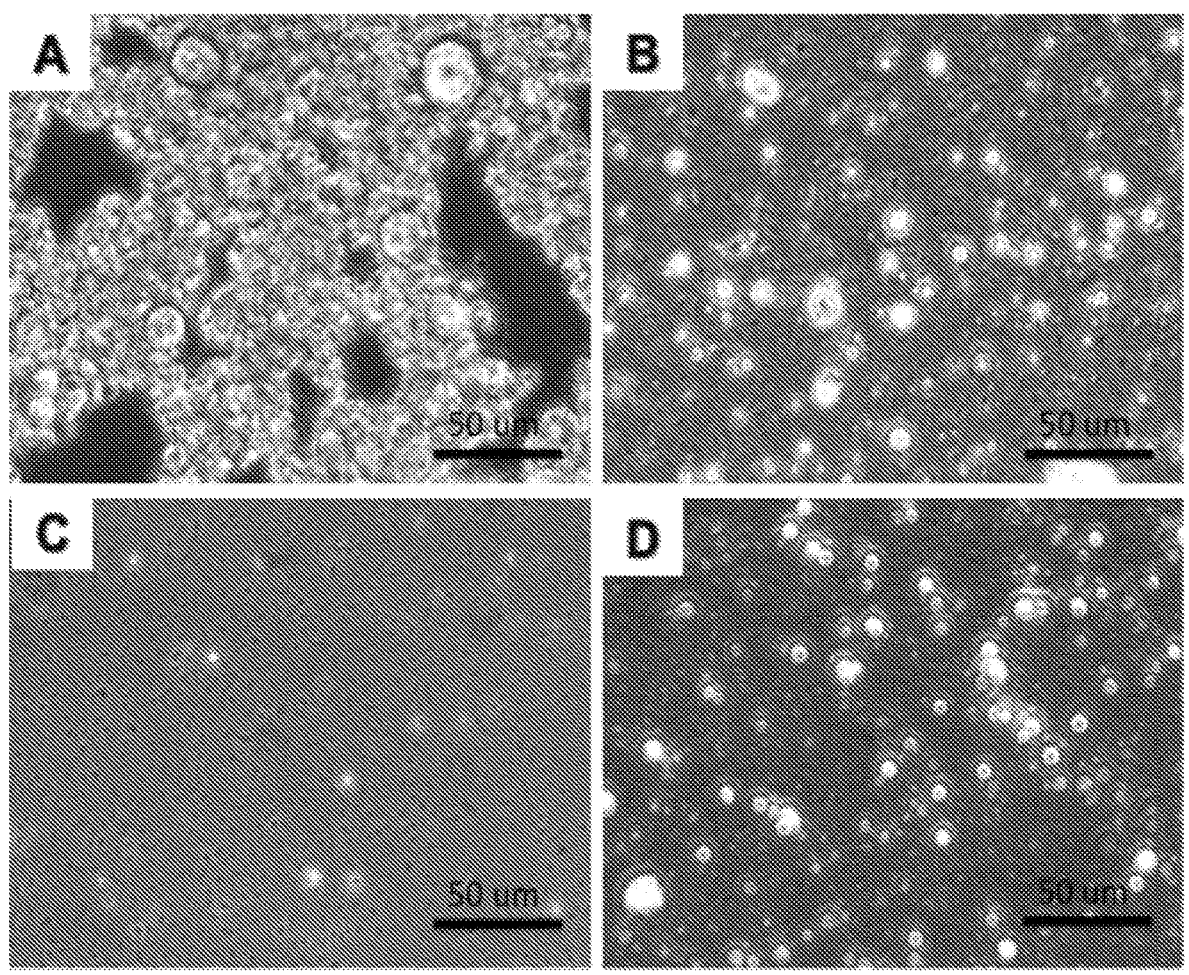
FIGS. 2A-2D are microscopic images of silk microspheres prepared by using 1,2-dioleoyl-sn-glycero-3-phosphocholine (DOPC) as a template.

Any art-recognized methods for fabrication of silk microspheres can be used for the purposes described herein. Silk microspheres prepared by two different aqueous-based methods, i.e., DOPC template and PVA phase separation, were used in this particular Example [20, 21]. In the preparation using DOPC, the method described in Ref 21 was modified to narrow the size distribution of the obtained microspheres while remain the DOPC coating (template) on silk microspheres. This was achieved by introducing a sonication treatment on the silk-DOPC mixture, followed by centrifugation to separate the DOPC-coated and uncoated microspheres, considering that, wishing to be bound by theory, the DOPC-coated fraction is lighter than the uncoated fraction. When the thin DOPC film in the glass tube was hydrated with silk solution, the mixture contained inhomogeneous vesicles, e.g., DOPC multilamellar vesicles that encapsulated silk microspheres (FIG. 2A). The big vesicles in the mixture broke up when subjected to sonication treatment, forming vesicles more homogeneous in size (FIG. 2B). This is similar to the effect of freeze-thaw cycles used in the previous report [21]. In some embodiments, without wishing to be bound by theory, sonication can also induce silk structural change from random coil to beta-sheet structure, forming a semi-solid gel in the vesicle, as reported in Ref. [23]. The following centrifugation step separated small particles (e.g., 1-2 μm) from the big ones (e.g., 5-10 μm) in the mixture (FIGS. 2C and 2D), both of which were subjected to friction tests as described in Example 1.

Figure 3A:
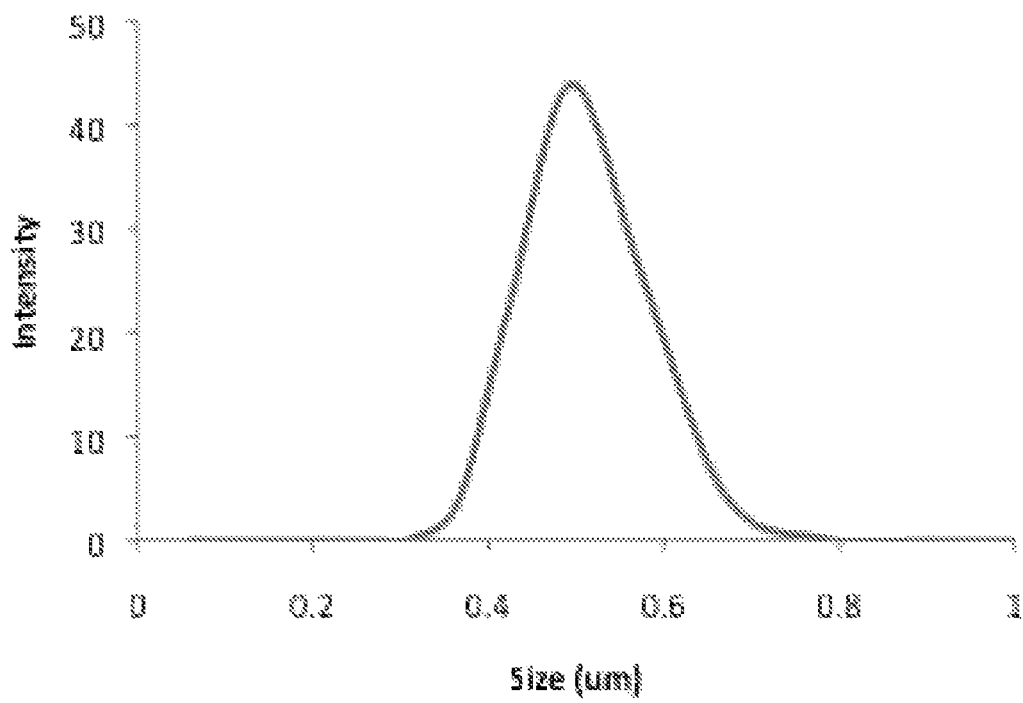
FIGS. 3A-3B are plots showing size distribution of silk micron- and nanoparticle species prepared by polyvinyl alcohol (PVA) phase separation method after a centrifugal separation step, determined by light scattering technique.
Figure 3B:
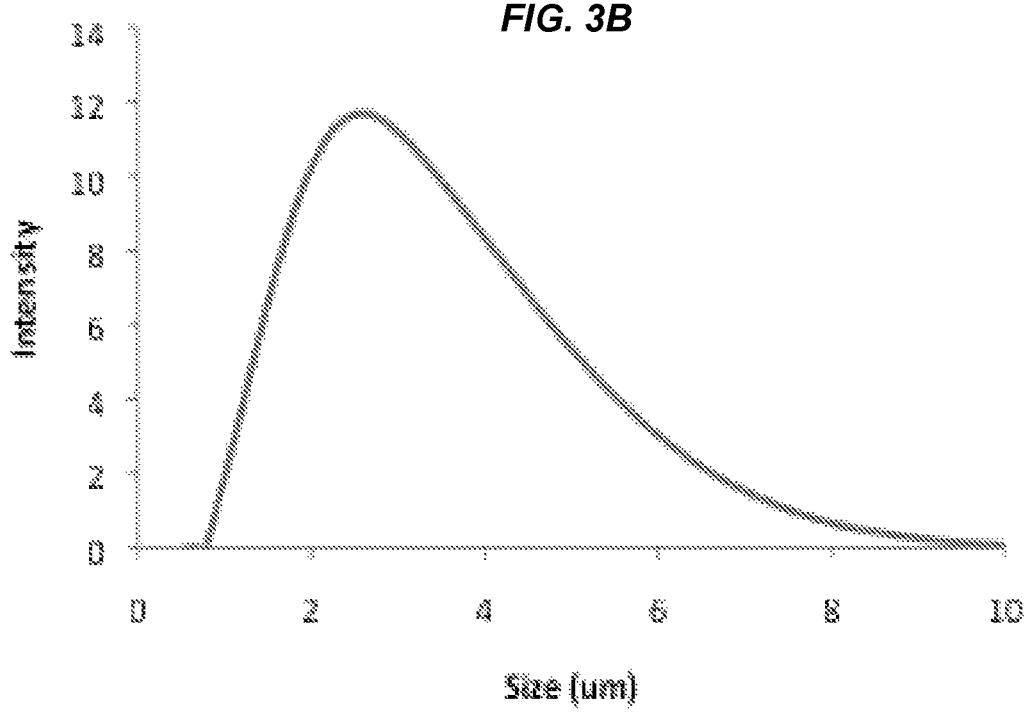

In the preparation using PVA, more than 95% PVA were removed by centrifugation at a high-speed, as reported in Ref [20]. Centrifugation at a lower speed was subsequently used to separate the particles with sizes of 0.5-1 μm from those bigger than 1 μm. The separation was then evaluated by light-scattering technique to determine the size distribution of particles at sub-micron and micron ranges (FIGS. 3A-3B). The size of sub-micron species (approximately 0.5 μm) was determined to be slightly larger than those obtained in the previous report (approximately 0.3 μm) [20]. Without wishing to be bound by theory, the difference in the particle size can be due to the difference in preparation of the silk microspheres. In the previous report [20], the silk and PVA mixture after sonication was air-dried to form a film, while in this Example the mixture after sonication was lyophilized. Without wishing to be bound by theory, in some embodiments, lyophilization can generate silk particles with a more porous structure and thus a larger volume, as compared to those prepared by the air-drying method.

DOPC Coating on PVA-Silk Microspheres.

Figure 4A:
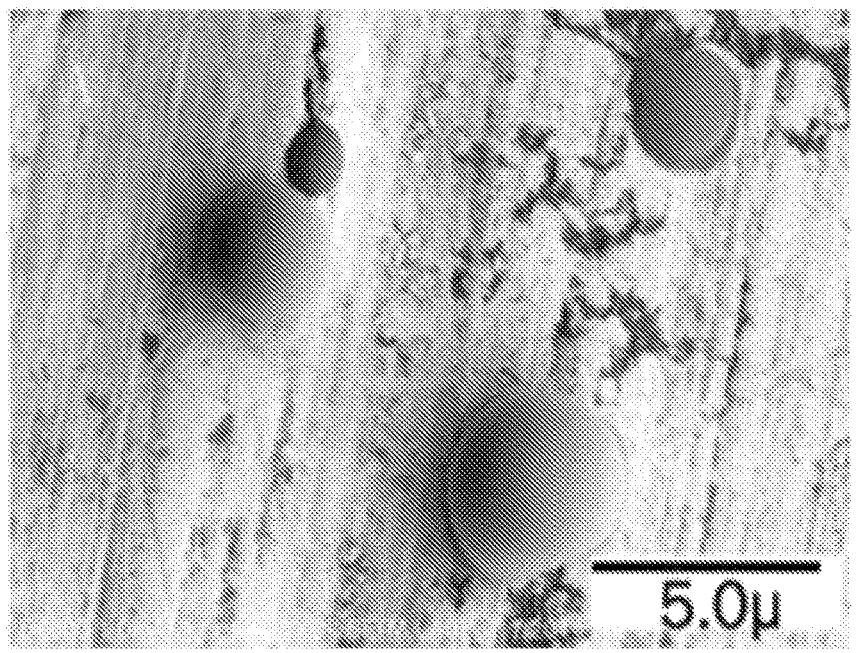
FIGS. 4A-4B are SEM images of silk microspheres that were prepared using PVA phase separation method and further coated with DOPC (1.25 wt %).
Figure 4B:
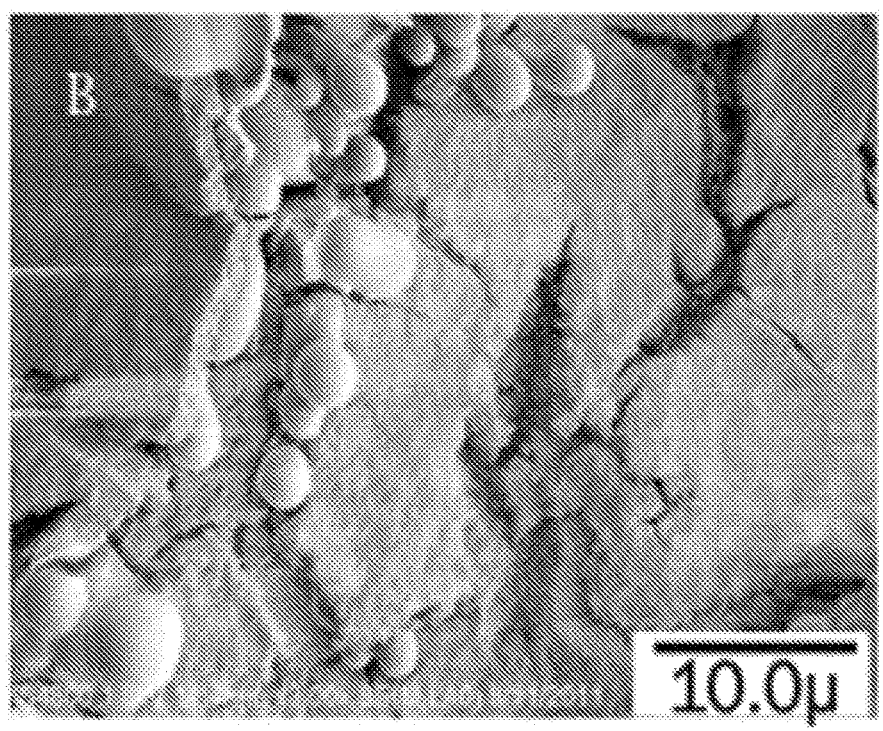

The silk microspheres prepared using PVA method, in some embodiments, were further coated with DOPC (post-prep coating) for comparison with those prepared using DOPC as a template, which had DOPC coating through the preparation (in-prep coating). Post-prep DOPC coating resulted in a smooth layer outside the silk microspheres, as indicated by SEM (FIGS. 4A-4B). The two kinds of coated microspheres (in-prep and post-prep coated) can differ in silk properties, with the later more solid and containing more beta-sheet structure than the former. This was indicated in the friction tests where the two kinds of microspheres showed different lubrication effects (see Example 3).

Example 3

Friction Testing for DOPC Coated Silk Microspheres

In friction tests, friction coefficients were determined when silk microspheres and DOPC-coated microspheres were added to the bath in which the two opposing surfaces were immersed (FIG. 1). The results were listed in Table 1 as below.

TABLE 1

Preparation and lubrication properties of silk microspheres

| Sample | Preparation | Original mixture | Particle size range | Friction coefficient |
|---|---|---|---|---|
| LS | DOPC-silk mixture, sonication treatment, no centrifugation | 20 wt % DOPC/8 wt % silk | 1-20 μm | 0.05 |
| LS-S | DOPC-silk mixture, sonication treatment, supernatant after centrifugation | 20 wt % DOPC/8 wt % silk | 1-2 μm | 0.04 |
| LS-P | DOPC-silk mixture, sonication treatment, resuspended pellet after centrifugation | 20 wt % DOPC/8 wt % silk | 5-10 μm | 0.1 |
| PS | PVA-silk mixture, resuspended pellet after centrifugation | 4 wt % PVA/1 wt % silk | 0.5-5 μm | 0.3 (0.03) |
| PS-S | PVA-silk mixture, supernatant after centrifugation | 4 wt % PVA/1 wt % silk | 0.5-1 μm | 0.22 (0.06) |
| PS-P | PVA-silk mixture, resuspended pellet after centrifugation | 4 wt % PVA/1 wt % silk | 1-5 μm | 0.24 (0.03) |

Note:
(1) Friction coefficients in the parentheses were determined after the coating of microspheres by DOPC at the condition described in Example 1.
(2) Sample PS-P (in bold) is used for DOPC coating and the cushion and wearing-protection experiments described in Example 4.

For the silk microspheres prepared using DOPC as a template, the friction coefficient of the small particle fractions (LS-S, 1-2 μm) was about 0.04, which is close to the original DOPC-silk mixture before centrifugation (LS). Without wishing to be bound by theory, small particles can dominate the DOPC-silk mixture, and they can be coated with relatively thick DOPC layers, which can effectively reduce boundary friction. In contrast, the big silk particles that are present in the pellet after centrifugation can be coated with thinner or no DOPC layer, thus showing a higher friction coefficient (0.1). The role of DOPC in facilitating lubrication was also shown in the PVA-based silk microspheres. In the absence of DOPC coating, the samples being assessed showed high friction coefficients at 0.2-0.3, indicating that silk microspheres alone, in some embodiments, do not have sufficient lubrication properties, as compared to the DOPC-coated samples (Tables 1 and 2). After coated with DOPC, the friction coefficients of the samples dropped significantly (numbers in the parentheses in Table 1), close or even lower than that of DOPC liposome alone (0.055, Table 2).

As shown in Table 1, the lowest friction coefficient (0.03) was achieved in the sample of resuspended pellet after centrifugation, while the supernatant fraction from the same centrifugation showed a higher value (0.06). Without wishing to be bound by theory, this can be due to the effect of rolling friction, as the resuspended pellet generally contained relatively large spheres (1-5 μm), which can be more effective than the particles with sub-micron size (0.5-1 μm) when functioning as rolling elements between the surfaces for reducing friction.

The role of DOPC coating was further assessed in a separate friction test experiment with additional samples. The results are shown in Table 2.

TABLE 2

Preparation and lubrication properties of DOPC-coated silk microspheres prepared using the PVA method

| Sample | Preparation | Original mixture | Friction coefficient |
|---|---|---|---|
| Water | Ultrapure water used as a control | 0 wt % DOPC/0 wt % silk | 0.16-0.193 |
| DOPC | DOPC liposomes | 1.25 wt % | 0.055-0.059 |
| DOPC | DOPC liposomes | 0.14 wt % | 0.17 |
| SM | Silk microspheres | 0.5 wt % | 0.172-0.21 |
| DOPC-SM | Silk microspheres with DOPC coating | 1.25 wt % DOPC/0.5 wt % silk | 0.03-0.04 |
| Supernatant | Supernatant collected after at least 3 washes of the DOPC-coated silk microspheres | N/A | 0.15 |
| W-DOPC-SM | DOPC-coated silk microspheres after water washing | 1.25 wt % DOPC/0.5 wt % silk | 0.04-0.056 |
| WM-DOPC-SM | Coated silk microspheres after water and methanol washing | 1.25 wt % DOPC/0.5 wt % silk | 0.18 |

As shown in Table 2, silk microspheres without coating (SM) showed a high friction coefficient (0.21), while the DOPC-coated microspheres (DOPC-SM) showed a much lower friction coefficient (0.03), consistent with that shown in Table 1. When the sample DOPC-SM was further washed with water, it resulted in a slight increase in friction coefficient (0.056), indicating that a small fraction of DOPC coating had been removed. When these microspheres were further washed with methanol, the friction coefficient increased dramatically to 0.18, similar to the uncoated silk microspheres, indicating that the DOPC coating was almost completely or completely removed from the microspheres.

The DOPC concentration used for coating can be optimized by measuring the friction coefficients of silk microparticles coated with different DOPC concentration. In some embodiments, it was determined that the friction coefficient of DOPC-coated silk microparticles reached lowest level when the DOPC concentrations were higher than 1.2 wt % (FIG. 5). In one embodiment, the DOPC concentration of 1.25 wt % was used for all the coatings in the Examples described herein.

Example 4

Anti-Wearing Effect of DOPC-Coated Silk Microspheres

Figure 7A:
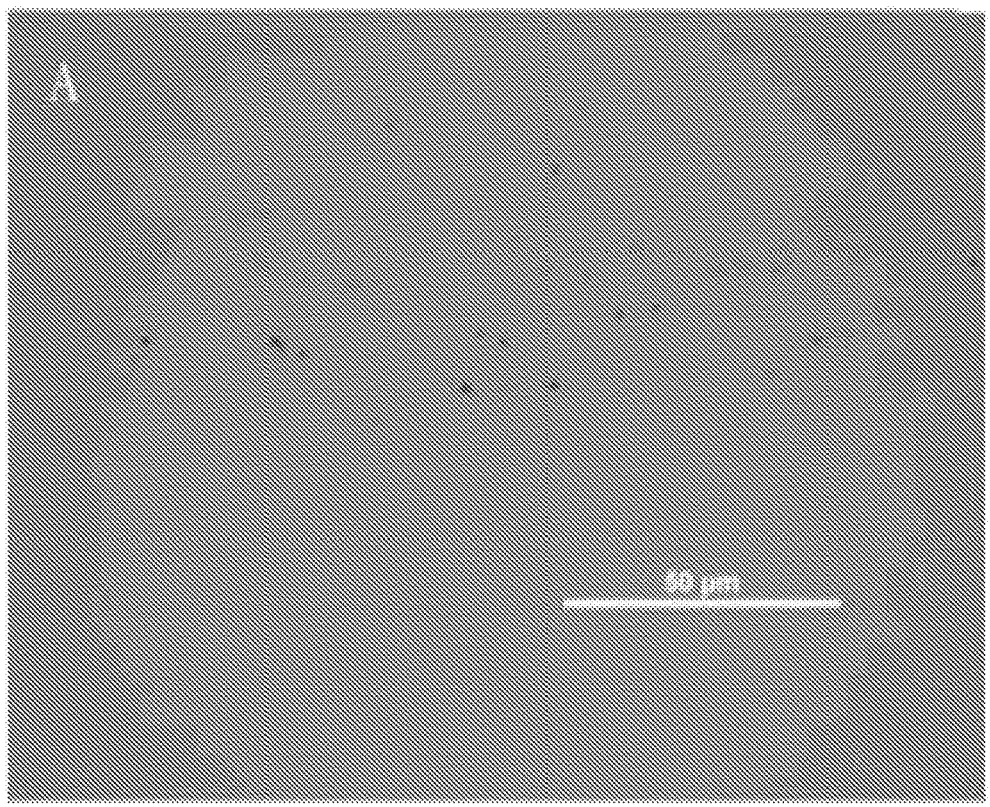
FIGS. 7A-7B are microscopic images of the wear pattern formed after shearing a glass probe against a silicon surface at 1.96 N (200 g) load for 50 cycles in the presence of (FIG. 7A) DOPC liposome as the lubricant, or (FIG. 7B) DOPC coated silk microspheres suspension as the lubricant.
Figure 7B:
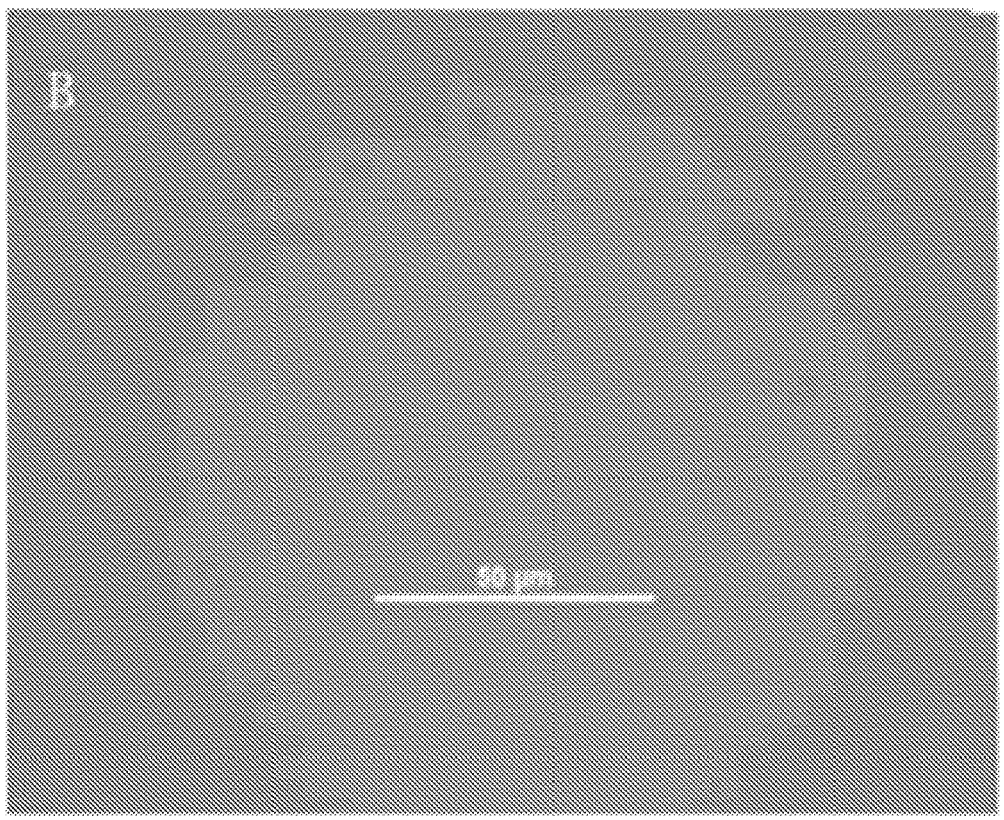
Figure 8:
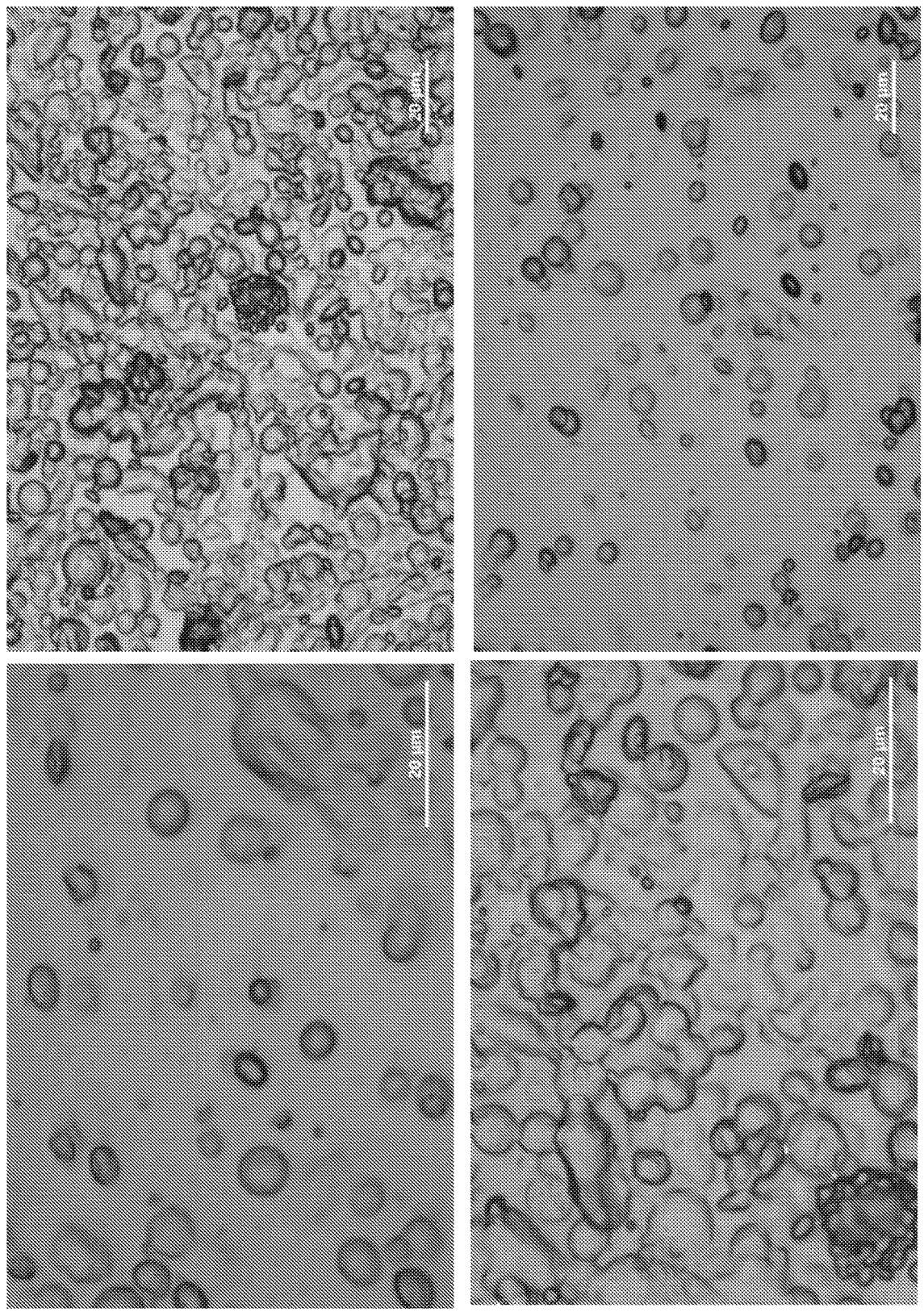
FIG. 8 is a set of microscopic images of DOPC-coated silk microspheres.
Figure 9:
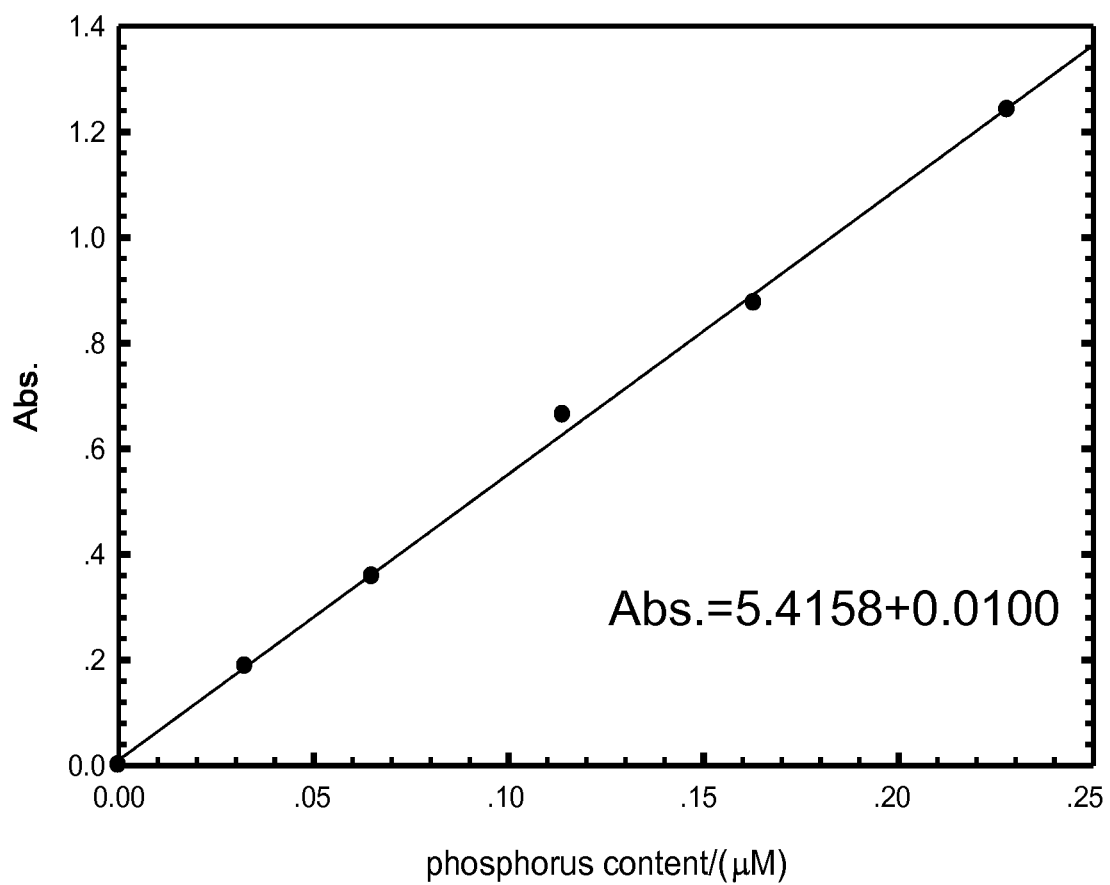
FIG. 9 is a standard curve for phosphorous content by UV-Vis. The concentration of DOPC lipid in coated silk microspheres after water wash was about 0.1401 wt %.
Figure 10:
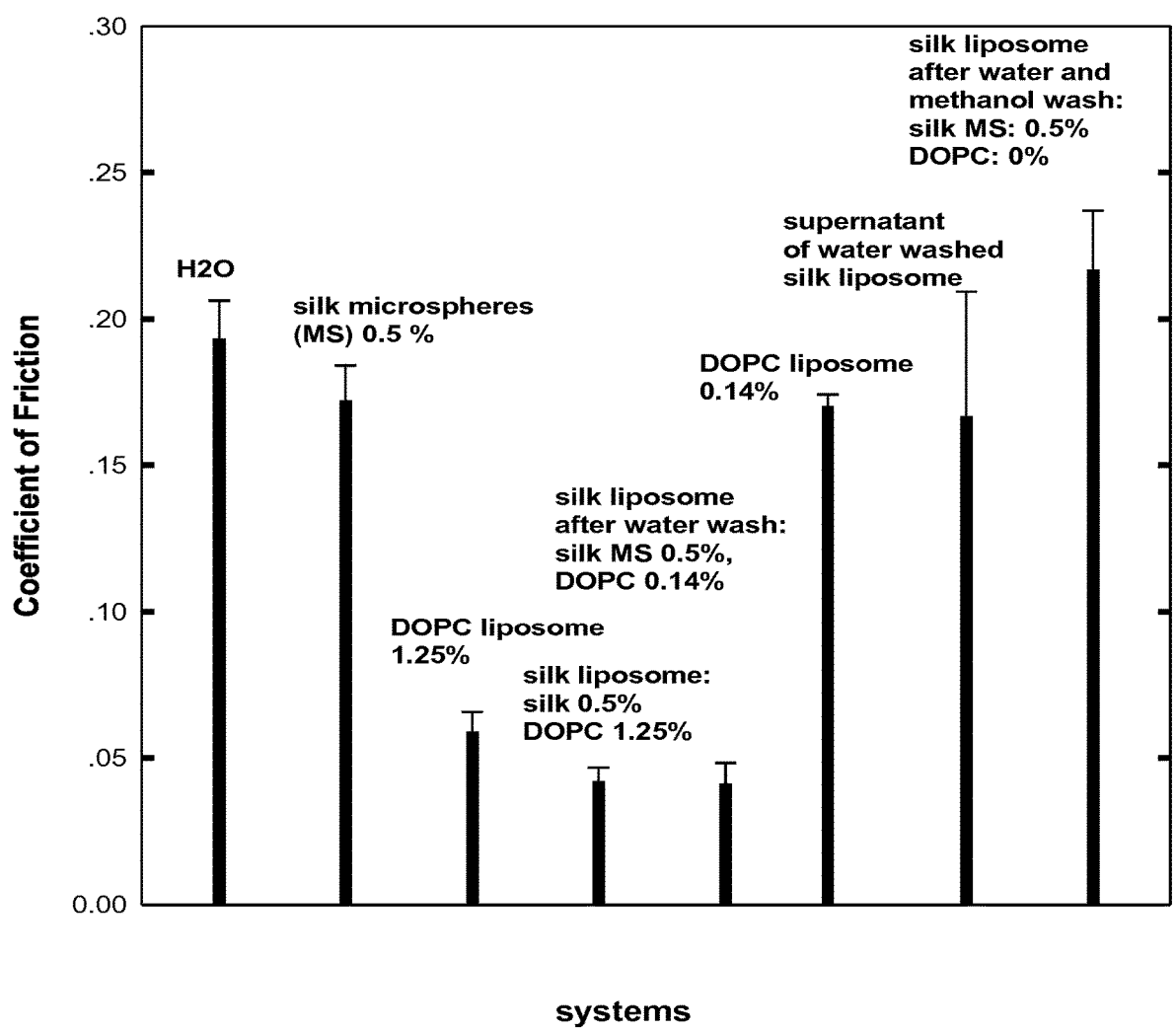
FIG. 10 is a plot showing coefficients of friction (COF) between glass tip and silicon wafers lubricated by different systems. All measurements were performed with an increasing load from about 0.196N (~20 g) to about 2.45N (~250 g), a sliding velocity of about 1 mm/s, and a dwell time of about 5 seconds.
Figures 11A, 11B:
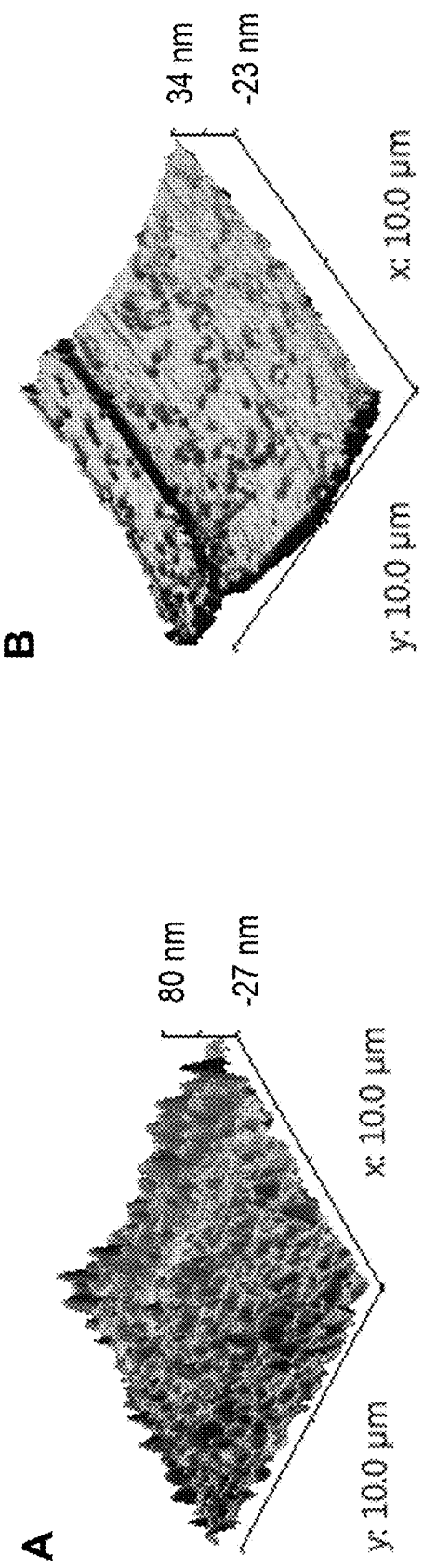
FIGS. 11A-11B is a set of AFM images of a wear pattern formed after shearing a glass probe against a silicon surface at 1.96N (~200 g) load for about 50 cycles in the presence of (FIG. 11A) DOPC liposome as the lubricant, or (FIG. 11B) DOPC lipid-coated silk microsphere suspension as the lubricant.
Figure 12A:
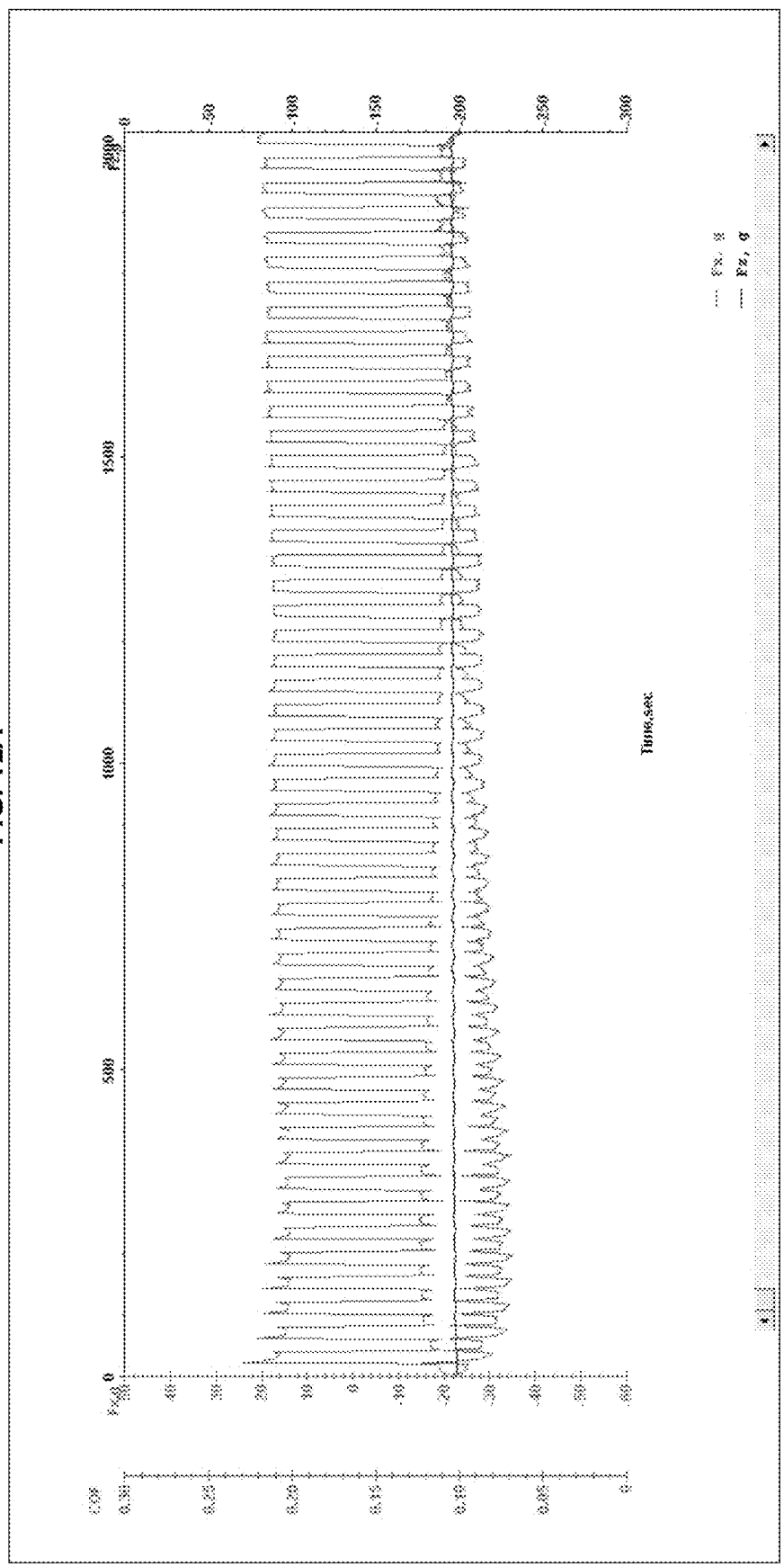
FIGS. 12A-12B are plots of typical friction force Fx, applied load Fz and coefficient friction (COF) trace versus time while shearing a spherical glass probe against a silicon surface at a load of about 1.96N (~200 g) for about 50 cycles in the presence of DOPC liposome (FIG. 12A) as the lubricant, or DOPC lipid-coated silk microspheres suspension (FIG. 12B) as the lubricant.
Figure 12B:
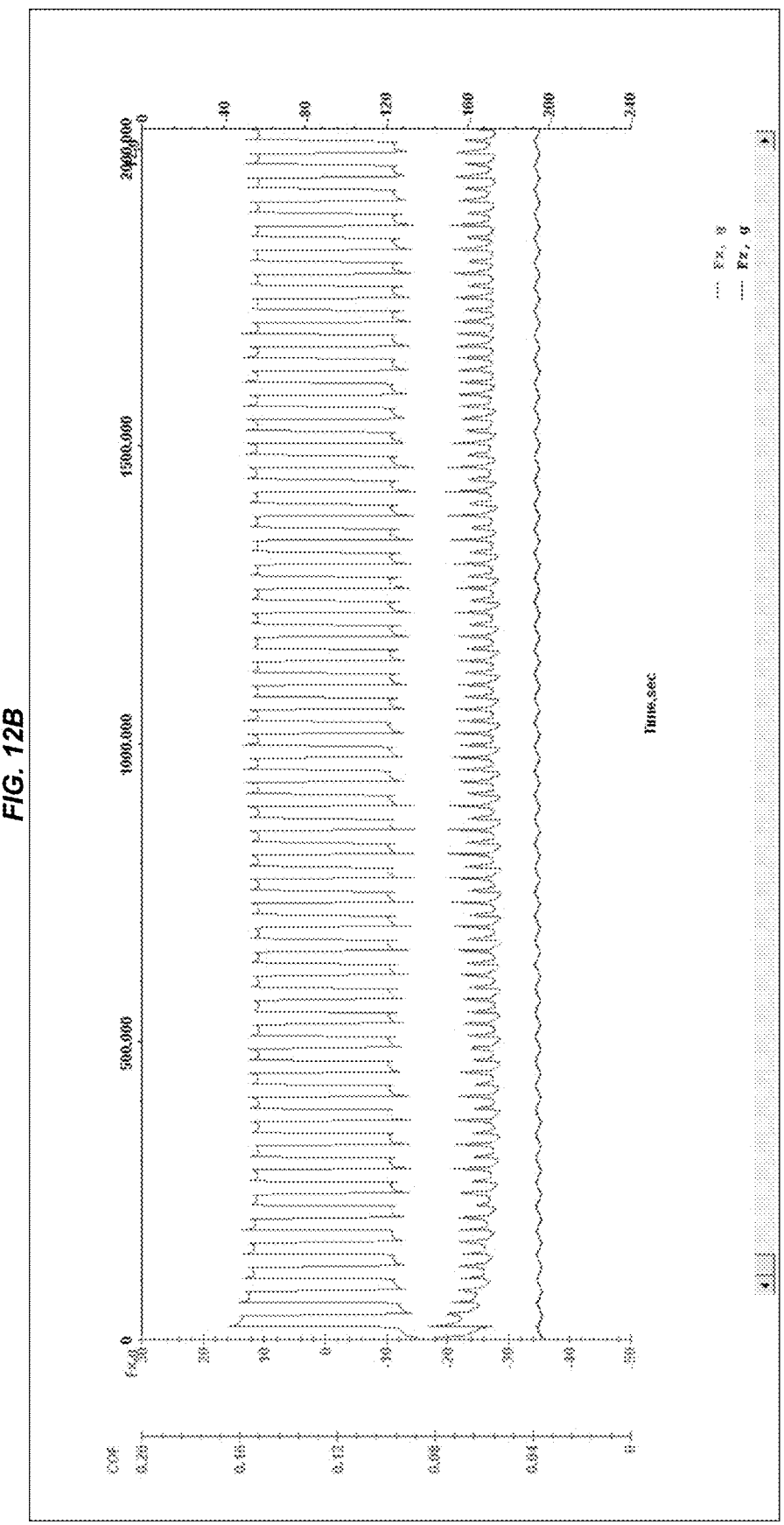
Figure 13A:
FIGS. 13A-13B are microscopic images of a wear pattern formed after shearing a glass probe against a silicon surface at 0.49 N (~50 g) load for about 500 cycles in the presence of (FIG. 13A) DOPC liposome as the lubricant, or (FIG. 13B) DOPC-coated silk microspheres suspension as the lubricant.
Figure 13B:
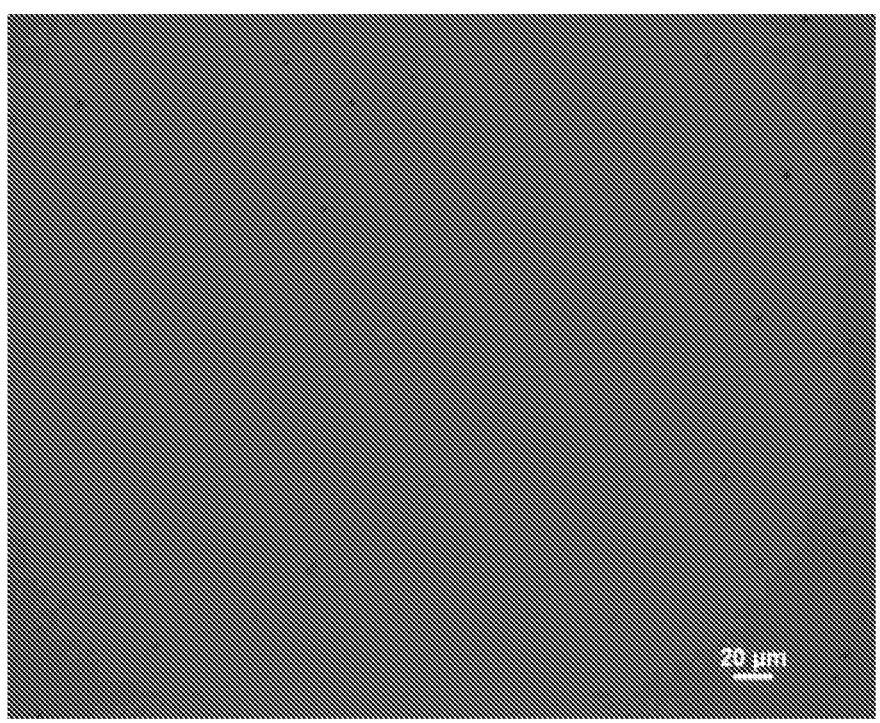
Figures 14A, 14B:
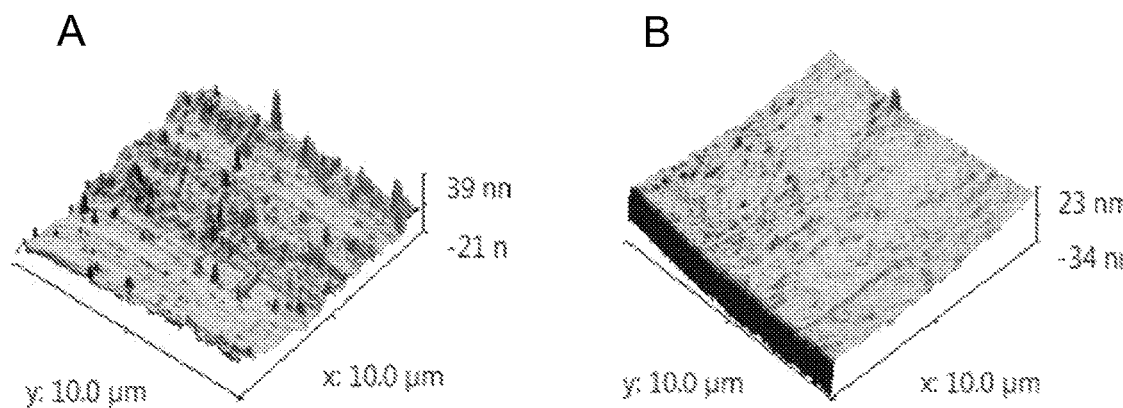
FIGS. 14A-14B is a set of AFM images showing a wear pattern formed after shearing a glass probe against a silicon surface at 0.49N (~50 g) load for about 500 cycles in the presence of (FIG. 14A) DOPC liposome as the lubricant, or (FIG. 14B) DOPC lipid-coated silk microsphere suspension as the lubricant.
Figure 15:
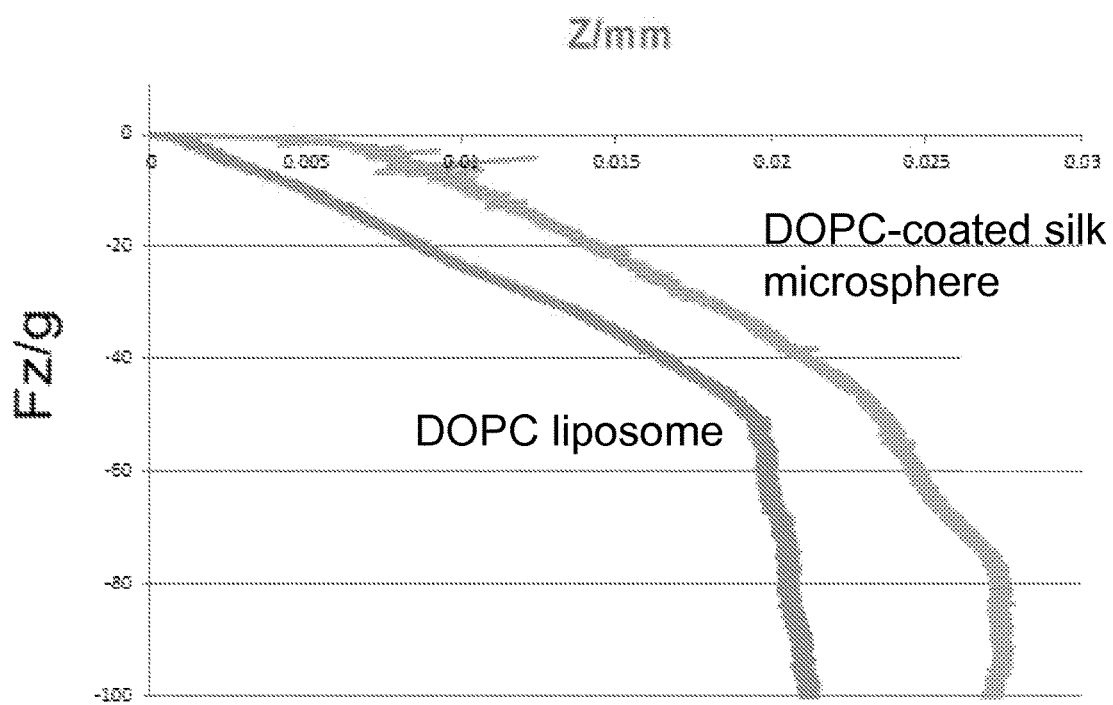
FIG. 15 is a plot showing cushion effect of DOPC liposome or DOPC-coated silk microspheres.

In the friction tests, the friction pattern derived from DOPC-coated silk microspheres was different from that of DOPC liposome alone, as shown in FIGS. 6A-6B. The stiction spicks in the friction trace were less prevalent when the DOPC-coated silk microspheres were used for lubrication as compared to the sample of DOPC liposome in the absence of silk (FIGS. 6A-6B), indicating that the presence of silk microspheres improved the surface cushion, e.g., by a mechanism of rolling friction. In some embodiments, the DOPC-coated silk microspheres can be tuned to provide a cushion effect that can last for a desired amount of time, e.g., days, weeks, months, or years. The presence of silk microspheres effectively prevented the surfaces from wearing. For example, when DOPC liposome was used, a wear pattern on the silicon surface was clearly visible under the microscope (FIG. 7A). In contrast, no significant or detectable wear pattern could be observed on the surface when DOPC-silk microspheres were used (FIG. 7B).

Silk microspheres can be coated by DOPC with different means, either in-preparation or post-preparation. DOPC-coated silk microspheres can function as a cushioning lubricant to reduce the friction between any contacted surfaces, e.g., through a mechanism of rolling friction, and can further prevent surface wearing in a long term application, at least partly due to the robust material property of silk. The combination of silk and phospholipids can act as a novel lubricant for any surfaces, including non-biological surfaces and biological surfaces. In some embodiments, the combination of silk and phospholipids can act as a novel joint lubricant, e.g., for treatment of joint disorders such as arthritis.

REFERENCES

[1] Corti, M. C.; Rigon, C. Aging Clin. Exp. Res. 2003; 15:359-363
[2] Grainger, R.; Cicuttini, F. M. Med. J. Aust. 2004; 180:232-236.
[3] Abate, M.; Pelotti, P.; J. Med. Sci. 2008; 113:261-278.
[4] Benz, M.; Chen, N. J. Biomed. Mater. Res., Part A 2004; 71:6-15.
[5] Swann, D. A.; Hendren, R. B.; Radin, E. L.; Sotman, S. L.; Duda, E. A. Arthritis Rheum. 1981; 24:22-30.
[6] Swann, D. A.; Mintz, G. Biochem. J. 1979; 179:465-471.
[7] Swann, D. A.; Slayter, H. S.; Silver, F. H. J. Biol. Chem. 1981; 256:5921-5925.
[8] Schwarz, I. M.; Hills, B. A. Br. J. Rheumatol. 1998; 37:21-26.
[9] Sarma, A. V.; Powell, G. L.; LaBerge, M. J. Orthoped. Res. 2001; 19:671-676.
[10] Vecchio, P.; Thomas, R.; Hills, B. A. Rheumatology 1999; 38:1020-1021.
[11] Oloyede, A.; Gudimelta, O. A.; Crawford, R.; Hills, B. A. Clin. Biomech. 2004; 19:534-542.
[12] Watanabe, M.; Leng, C. G.; Toriumi, H.; Hamada, Y.; Akamatsu, N.; Ohno, S. Med. Electron Microsc. 2000:33; 16-24.
[13] Kawano, T.; Miura, H.; Mawatari, T.; Moro-Oka, T.; Nakanishi, Y.; Higaki, H.; Iwamoto, Y. Arthritis Rheum. 2003; 48:1923-1929.
[14] Sivan, S.; Schroeder, A.; Verberne, G.; Merkher, Y.; Diminsky, D.; Priev, A.; Maroudas, A.; Halperin, G.; Nitzan, D.; Etsion, I.; Barenholz, Y. Langmuir 2010; 26:1107-1116
[15] Altman, G. H.; Diaz, F.; Jakuba, C.; Calabro, T.; Horan, R. L.; Chen, J.; Lu, H.; Richmond, J.; Kaplan, D. L. Biomaterials 2003; 24:401-416.
[16] Kaplan, D. L.; Adams, W.; Farmer, B.; Viney, C. Silk polymers: materials science and biotechnology. Washington D.C.: American Chemical Society; 1994.
[17] Gupta, V.; Aseh, A.; Ríos, C N.; Aggarwal, B. B.; Mathur, A. B. Int. J. Nanomedicine 2009; 4:115-122.
[18] Hino, T.; Shimabayashi, S. Pharmacy Pharmacol. Commun. 2000; 6:335-339.
[19] Zhang, Y. Q.; Shen, W. D.; Xiang, R. L.; Zhang, L. J.; Gao, W. J.; Wang, W. B. J. Nanoparticle Res. 2007; 9:885-900.
[20] Wang, X.; Yucel, T.; Lu, Q.; Hu, X.; Kaplan, D. L. Preparation of Biomaterials 2010; 31, 1025-1035.
[21] Wang, X.; Wenk, E.; Matsumoto, A.; Meinel, L.; Li, C.; Kaplan, D. L. J. Control. Release 2007; 117:360-370.
[22] Sofia, S.; McCarthy, M. B.; Gronowicz, G.; Kaplan, D. L. J. Biomed. Mater. Res. 2001; 54:139-148.
[23] Wang, X.; Kluge, J. A.; Leisk, G. G.; Kaplan, D. L. Biomaterials 2008; 29:1054-1064.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A lubricated microsphere comprising:
   a silk fibroin microsphere comprising
      one or more pores having a pore size range of 1 nm to 100 μm,
      wherein the silk fibroin is free of lipid; and
   a phospholipid coating on a surface of the silk fibroin microsphere,
      wherein when the lubricated microsphere is under a cyclic shear loading pressure of at least 0.08 MPa for at least a week, the lubricated microsphere resist degradation, and
      wherein the lubricated microsphere is characterized by a static friction coefficient of less than 0.1, as determined by a friction test against a silica surface.

2. The lubricated microsphere of claim 1, wherein the lubricated microsphere has a width dimension of about 1 μm to about 100 μm.

3. The lubricated microsphere of claim 1, wherein the lubricated microsphere has a width dimension of at least about 3 μm or higher.

4. The lubricated microsphere of claim 1, wherein an amount of the phospholipid coating present on the lubricated microsphere ranges from about 0.01 wt % to about 10 wt %.

5. The lubricated microsphere of claim 1, wherein the phospholipid coating comprises one or more phospholipids.

6. The lubricated microsphere of claim 1, wherein the lubricated microsphere further comprises an additive or active agent.

7. The lubricated microsphere of claim 6, wherein the additive or active agent is present in and/or on the phospholipid coating, the silk microsphere, or a combination thereof.

8. The lubricated microsphere of claim 1, wherein the lubricated microsphere is substantially spherical.

9. The lubricated microsphere of claim 1, wherein the lubricated microsphere is formulated for use in a mammalian subject.

10. The lubricated microsphere of claim 9, wherein the lubricated microsphere is formulated for use as a joint lubricant.

11. A method comprising placing between a first biological surface and a second biological surface a lubricated microsphere of claim 1, thereby reducing friction between the first biological surface and the second biological surface.

12. A method of treating arthritis in a subject comprising placing between two joint surfaces in the subject a lubricated microsphere of claim 1, thereby reducing friction between the two joint surfaces.

13. A method of making a lubricated microsphere comprising:
    sonicating a mixture comprising
        silk fibroin microspheres,
            wherein the silk fibroin microspheres are free of lipid and
        a lipid composition, whereby the sonicating forms a suspension comprising lubricated microspheres that comprise the lipid composition coating a surface of the silk fibroin microsphere, wherein each silk fibroin microsphere of the lubricated microspheres comprises a pore having a pore size range of 1 nm to 100 μm, and
    wherein when the lubricated microsphere is under a cyclic shear loading pressure of at least 0.08 MPa for at least a week, the lubricated microsphere resists degradation.

14. The method of claim 13, wherein the concentration of the lipid composition in the mixture is about 5 wt % to about 50 wt %, or about 10 wt % to about 30 wt %.

15. The method of claim 13, wherein the concentration of the lipid composition in the mixture ranges from about 0.05% wt % to about 10 wt %.

16. A method of making a lubricated microsphere comprising a silk microsphere substantially free of lipid and a phospholipid coating lubricating a surface of the silk microsphere, the method comprising:

a. sonicating a mixture comprising a silk fibroin solution and a PVA solution wherein the silk fibroin solution is free of lipid;
   b. lyophilizing the mixture;
   c. dissolving the lyophilized mixture in an aqueous solution;
   d. removing at least a portion of the PVA, thereby forming a silk microsphere; and
   e. sonicating the silk microsphere with a hydrated lipid composition, thereby forming a lubricated microsphere, wherein each silk fibroin microsphere of the lubricated microspheres comprises a pore having a pore size range of 1 nm to 100 μm.

17. The method of claim 16, wherein the PVA solution has a concentration of about 1 wt % to about 10 wt %.

18. The method of claim 13, further comprising separating smaller-sized lubricated microspheres from larger-sized lubricated microspheres.

19. The method of claim 13, wherein the lipid composition comprises one or more phospholipids.

20. The method of claim 13, wherein the silk fibroin present in the silk fibroin microspheres is in an amount of at least 5%.

21. The method of claim 13, wherein the silk fibroin microspheres further comprise an additive or active agent.

22. A lubricated microsphere produced by the method of claim 13.

23. The method of claim 13, further comprising a step of lyophilizing at least a portion of the suspension.

24. The method of claim 16, where the volume ratio of the silk fibroin solution to the PVA solution is about 1:1 to about 10:1.

\* \* \* \* \*

UNITED STATES PATENT AND TRADEMARK OFFICE
CERTIFICATE OF CORRECTION

PATENT NO. : 10,653,786 B2
APPLICATION NO. : 14/390351
DATED : May 19, 2020
INVENTOR(S) : David L. Kaplan et al.

It is certified that error appears in the above-identified patent and that said Letters Patent is hereby corrected as shown below:

On the Title Page

Item (73) "Tulane Educational Fund" should be --The Administrators of the Tulane Educational Fund--.

Signed and Sealed this
Sixteenth Day of July, 2024

Katherine Kelly Vidal
*Director of the United States Patent and Trademark Office*